US012351623B2

United States Patent
El-Agnaf et al.

(10) Patent No.: US 12,351,623 B2
(45) Date of Patent: Jul. 8, 2025

(54) ANTIBODY COMPOSITIONS TARGETING NON-PHOSPHORYLATED ALPHA-SYNUCLEIN AGGREGATES

(71) Applicant: Qatar Foundation for Education, Science and Community Development, Doha (QA)

(72) Inventors: Omar El-Agnaf, Doha (QA); Nour Khaled Majbour, Doha (QA); Nishant Vaikath, Doha (QA)

(73) Assignee: HAMAD BIN KHALIFA UNIVERSITY, Doha (QA)

( * ) Notice: Subject to any disclaimer, the term of this patent is extended or adjusted under 35 U.S.C. 154(b) by 926 days.

(21) Appl. No.: 17/511,230

(22) Filed: Oct. 26, 2021

(65) Prior Publication Data

US 2022/0089708 A1  Mar. 24, 2022

Related U.S. Application Data

(63) Continuation-in-part of application No. PCT/QA2021/050019, filed on Sep. 17, 2021.

(60) Provisional application No. 63/079,767, filed on Sep. 17, 2020.

(51) Int. Cl.
*C07K 16/18* (2006.01)
*C12N 5/16* (2006.01)
*G01N 33/68* (2006.01)

(52) U.S. Cl.
CPC .............. *C07K 16/18* (2013.01); *C12N 5/163* (2013.01); *G01N 33/6896* (2013.01); *C07K 2317/14* (2013.01); *C07K 2317/34* (2013.01); *C07K 2317/565* (2013.01); *C07K 2317/76* (2013.01); *G01N 2800/2835* (2013.01)

(58) Field of Classification Search
CPC .......................... C07K 16/18; C07K 2317/14; C07K 2317/34; C07K 2317/565; C07K 2317/76; C07K 14/47; C07K 2317/32; C12N 5/163; G01N 33/6896; G01N 2800/2835
See application file for complete search history.

(56) References Cited

U.S. PATENT DOCUMENTS

| 8,092,801 | B2 | 1/2012 | Schenk et al. |
| 8,613,905 | B2 | 12/2013 | El-Agnaf |
| 8,632,776 | B2 | 1/2014 | Nordstrom et al. |
| 8,778,334 | B2 | 7/2014 | El-Agnaf et al. |
| 8,795,664 | B2 * | 8/2014 | Bayer .................... C07K 16/18 424/139.1 |
| 9,534,044 | B2 | 1/2017 | El-Agnaf |
| 10,208,111 | B2 | 2/2019 | El-Agnaf |
| 10,464,999 | B2 * | 11/2019 | Liu ........................ C07K 16/18 |
| 10,488,417 | B2 | 11/2019 | El-Agnaf |
| 10,548,984 | B2 | 2/2020 | El-Agnaf |
| 11,155,608 | B2 * | 10/2021 | Luk ......................... A61P 25/28 |

FOREIGN PATENT DOCUMENTS

WO  WO-2005047860 A2 *  5/2005  ............. C07K 16/18

OTHER PUBLICATIONS

Preliminary Report on Patentability for related International Application No. PCT/QA2021/050019 action dated Mar. 21, 2023; (8 pages).

* cited by examiner

*Primary Examiner* — Anand U Desai
*Assistant Examiner* — Kathleen Cunningchen
(74) *Attorney, Agent, or Firm* — K&L Gates LLP

(57) ABSTRACT

The present specification provides a monoclonal antibody that specifically binds aggregated, non-phosphorylated α-synuclein and a hybridoma producing it. Also disclosed are methods of generating antibodies that specifically binds aggregated, non-phosphorylated α-synuclein and uses thereof. Uses of anti-α-synuclein antibody in detection and diagnostic assays, and for prophylaxis or therapy of α-synuclein-associated neurodegenerative diseases, are also disclosed.

4 Claims, 15 Drawing Sheets

Specification includes a Sequence Listing.

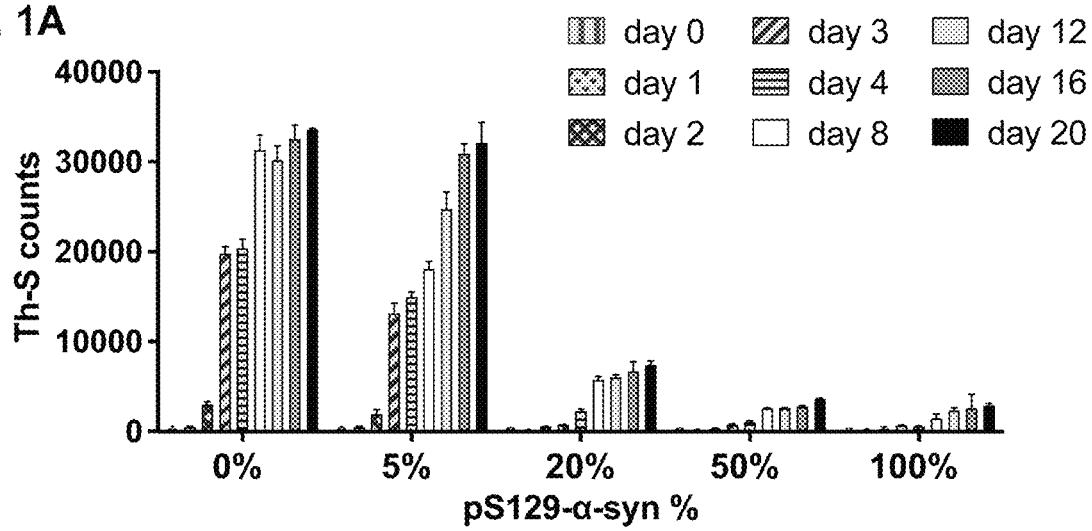
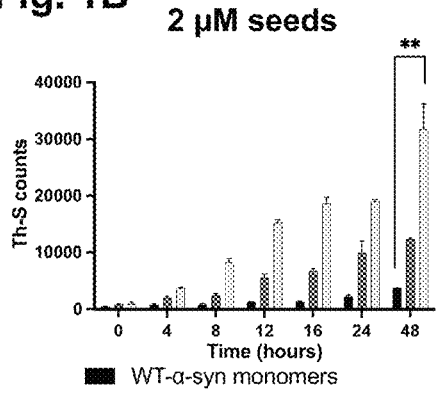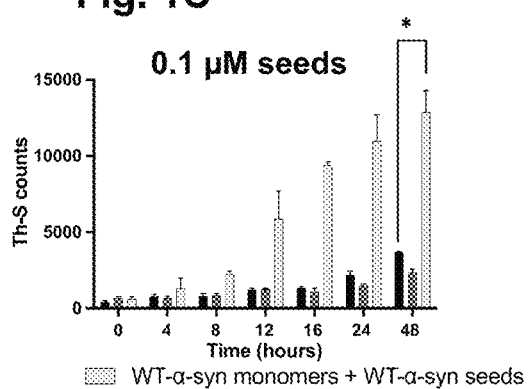
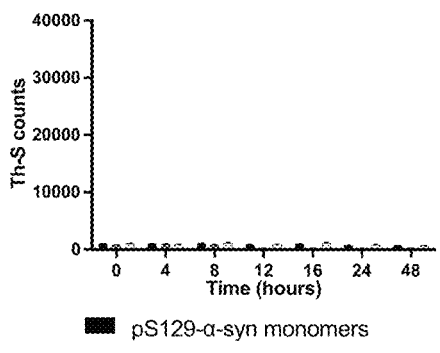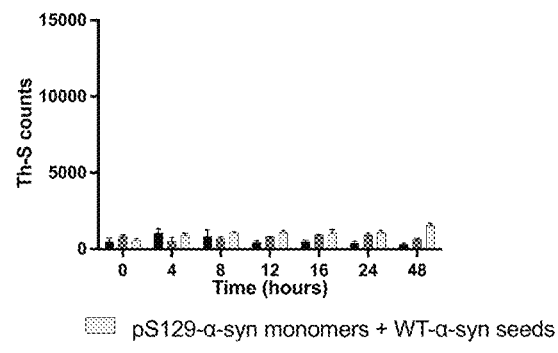

Fig. 6
Fig. 6A
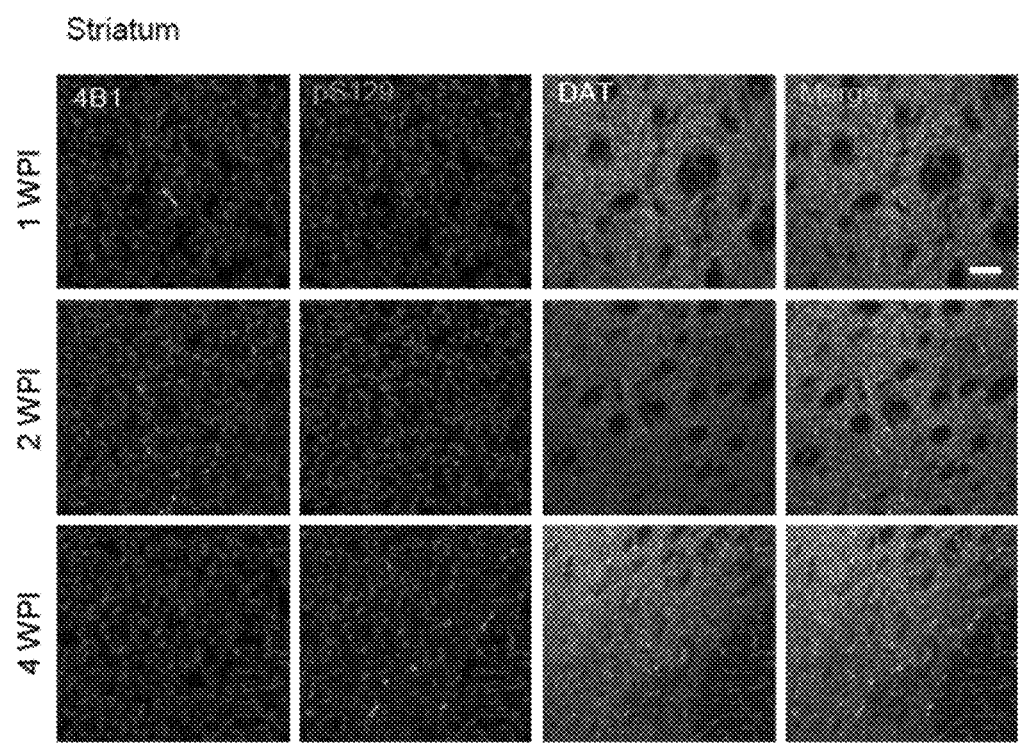
Fig. 6B
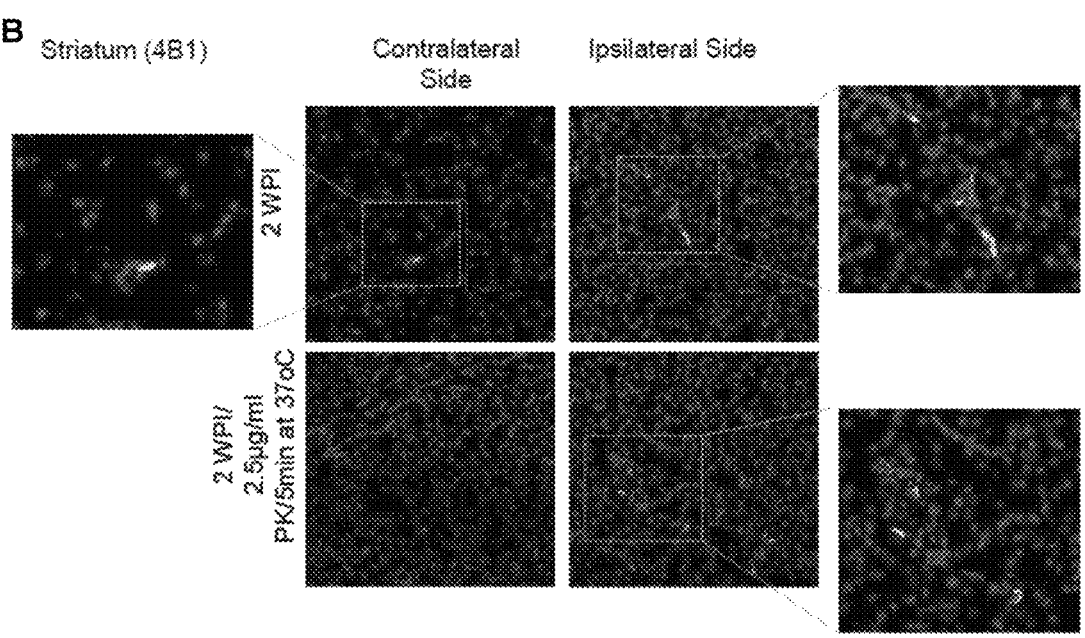

- ● WT-α-syn pure fibrils
- ■ WT-α-syn pure fibrils + WT-α-syn monomers
- ▼ WT-α-syn pure seeds + WT-α-syn monomers
- ▲ WT-α-syn pure seeds

- ● WT-α-syn monomers
- ■ WT-α-syn pure fibrils + WT-α-syn monomers
- ▲ WT-α-syn pure seeds + WT-α-syn monomers 1, Recombinant α-syn; 2, Non transfected cell lysate; 3, Scrambled siRNA; 4, Reagent transfected; 5, siRNA transfected.

Fig. 12B
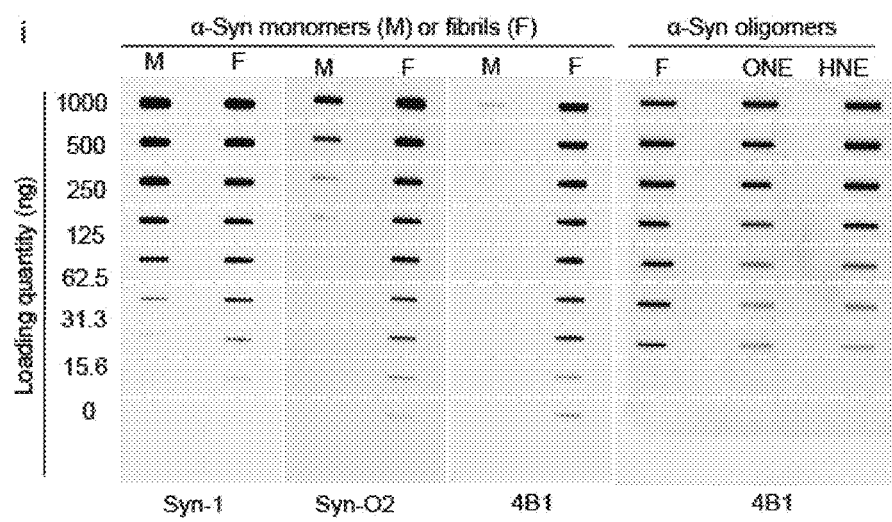
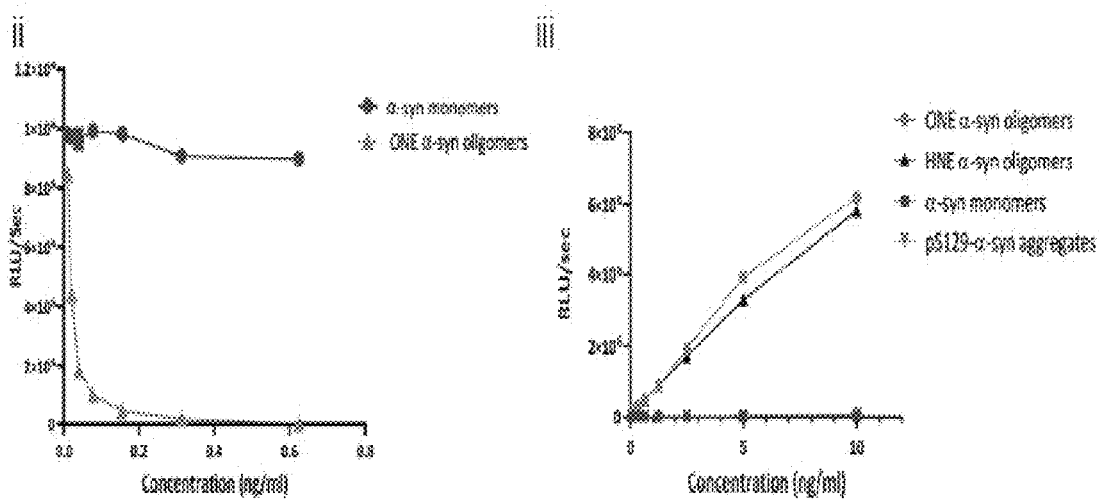

1, Control untreated; 2, Plasmid alone; 3, Seed alone; 4, Plasmid and seeds 6 hr; 5, Plasmid and seeds 12hr; 6, Plasmid and seeds 24 hr; 7, Plasmid and seeds 48 hr; 8, rpS129-α-syn; 9, rα-syn.

SEQUENCE LISTING

```
<160> NUMBER OF SEQ ID NOS: 15

<210> SEQ ID NO 1
<211> LENGTH: 112
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Glu Gly Tyr Gln Asp Tyr Glu Pro Glu Ala
            100                 105                 110

<210> SEQ ID NO 2
<211> LENGTH: 9
<212> TYPE: PRT
<213> ORGANISM: Homo sapiens

<400> SEQUENCE: 2

Tyr Glu Met Pro Ser Glu Glu Gly Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: SEQ ID NO:2 with a N terminal cysteine

<400> SEQUENCE: 3

Cys Tyr Glu Met Pro Ser Glu Glu Gly Tyr
1               5                   10

<210> SEQ ID NO 4
<211> LENGTH: 1401
<212> TYPE: DNA
<213> ORGANISM: Mus musculus

<400> SEQUENCE: 4
atgaatttcg ggctcagctt gatttccctt gtccctgttt taaaaggtgt cctgtgtgaa      60
gtgaaactgg tggagtctgg gggaggttta gtgcagcctg gagggtccct gaaactctcc     120
tgtgcagcct ctggaatcac tttcagtagc tataccatgt cttgggttcg ccagactcca     180
gagaagaggc tggagtgggt cggatatatt agtaatggtg gtggtaggac ctactatcca     240
```

-continued

```
gacactgtaa agggccgatt caccatctcc agagacaatg ccaagaacac cctgtacctg    300
caaatgagca gtctgaagtc tgaggacacg gccatgtatt actgtgcaag acagattact    360
acggctatgg ggtattacta tgctatggac tactggggtc aaggaacctc agtcaccgtc    420
tcctcagcca aaacgacacc cccatctgtc tatccactgg ccctggatc tgctgcccaa     480 actaactcca tggtgaccct gggatgcctg gtcaagggct atttccctga ccagtgaca     540 gtgacctgga actctggatc cctgtccagc ggtgtgcaca ccttcccagc tgtcctggag    600
tctgacctct acactctgag cagctcagtg actgtcccct ccagccctcg gcccagcgag    660
accgtcacct gcaacgttgc cacccggcc agcagcacca aggtggacaa gaaaattgtg     720
cccagggatt gtggttgtaa gccttgcata tgtacagtcc cagaagtatc atctgtcttc    780
atcttccccc caaagcccaa ggatgtgctc accattactc tgactcctaa ggtcacgtgt    840
gttgtggtag acatcagcaa ggatgatccc gaggtccagt tcagctggtt tgtagatgat    900
gtggaggtgc acacagctca gacgcaaccc cgggaggagc agttcaacag cactttccgc    960
tcagtcagtg aacttcccat catgcaccag gactggctca atggcaagga gttcaaatgc   1020
agggtcaaca gtgcagcttt ccctgccccc atcgagaaaa ccatctccaa aaccaaaggc   1080
agaccgaagg ctccacaggt gtacaccatt ccacctccca aggagcagat ggccaaggat   1140
aaagtcagtc tgacctgcat gataacagac ttcttccctg aagacattac tgtggagtgg   1200
cagtggaatg ggcagccagc ggagaactac aagaacactc agcccatcat gaacacgaat   1260
ggctcttact tcgtctacag caagctcaat gtgcagaaga gcaactggga ggcaggaaat   1320
actttcacct gctctgtgtt acatgagggc ctgcacaacc accatactga aagagcctc    1380 tcccactctc ctggtaaatg a                                             1401
```

<210> SEQ ID NO 5
<211> LENGTH: 466
<212> TYPE: PRT
<213> ORGANISM: Mus musculus

<400> SEQUENCE: 5

```
Met Asn Phe Gly Leu Ser Leu Ile Phe Leu Val Pro Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Ile Thr Phe
        35                  40                  45

Ser Ser Tyr Thr Met Ser Trp Val Arg Gln Thr Pro Glu Lys Arg Leu
    50                  55                  60

Glu Trp Val Gly Tyr Ile Ser Asn Gly Gly Gly Arg Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Gln Ile Thr Thr Ala Met Gly Tyr Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
```

```
                    165                 170                 175
Glu Pro Val Thr Val Thr Trp Asn Ser Gly Ser Leu Ser Ser Gly Val
                180                 185                 190

His Thr Phe Pro Ala Val Leu Gln Ser Asp Leu Tyr Thr Leu Ser Ser
            195                 200                 205

Ser Val Thr Val Pro Ser Ser Pro Arg Pro Ser Glu Thr Val Thr Cys
        210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asn Thr Asn Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 6
<211> LENGTH: 123
<212> TYPE: PRT
<213> ORGANISM: Mus musculus

<400> SEQUENCE: 6

Glu Val Lys Leu Val Glu Ser Gly Gly Gly Leu Val Gln Pro Gly Gly
1               5                   10                  15

Ser Leu Lys Leu Ser Cys Ala Ala Ser Gly Ile Thr Phe Ser Ser Tyr
            20                  25                  30

Thr Met Ser Trp Val Arg Gln Thr Pro Glu Lys Arg Leu Glu Trp Val
        35                  40                  45

Gly Tyr Ile Ser Asn Gly Gly Arg Thr Tyr Tyr Pro Asp Thr Val
    50                  55                  60
```

-continued

```
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Gln Ile Thr Thr Ala Met Gly Tyr Tyr Tyr Ala Met Asp Tyr
            100                 105                 110

Trp Gly Gln Gly Thr Ser Val Thr Val Ser Ser
            115                 120

<210> SEQ ID NO 7
<211> LENGTH: 8
<212> TYPE: PRT
<213> ORGANISM: Mus musculus

<400> SEQUENCE: 7

Gly Ile Thr Phe Ser Ser Tyr Thr
1               5

<210> SEQ ID NO 8
<211> LENGTH: 8
<212> TYPE: PRT
<213> ORGANISM: Mus musculus

<400> SEQUENCE: 8

Ile Ser Asn Gly Gly Gly Arg Thr
1               5

<210> SEQ ID NO 9
<211> LENGTH: 16
<212> TYPE: PRT
<213> ORGANISM: Mus musculus

<400> SEQUENCE: 9

Ala Arg Gln Ile Thr Thr Ala Met Gly Tyr Tyr Tyr Ala Met Asp Tyr
1               5                   10                  15

<210> SEQ ID NO 10
<211> LENGTH: 717
<212> TYPE: PRT
<213> ORGANISM: Mus musculus

<400> SEQUENCE: 10

Ala Thr Gly Ala Ala Gly Thr Thr Gly Cys Cys Thr Gly Thr Thr Ala
1               5                   10                  15

Gly Gly Cys Thr Gly Thr Thr Gly Gly Thr Gly Cys Thr Gly Ala Thr
            20                  25                  30

Gly Thr Thr Cys Thr Gly Gly Ala Thr Thr Cys Cys Thr Gly Cys Thr
        35                  40                  45

Thr Cys Cys Ala Gly Cys Ala Gly Thr Gly Ala Thr Gly Thr Thr Gly
    50                  55                  60

Thr Gly Ala Thr Gly Ala Cys Cys Cys Ala Ala Cys Thr Cys Cys Cys
65                  70                  75                  80

Ala Cys Thr Cys Thr Cys Cys Cys Thr Gly Cys Cys Thr Gly Thr Cys
                85                  90                  95

Ala Gly Thr Cys Thr Thr Gly Gly Ala Gly Ala Thr Cys Ala Ala Gly
            100                 105                 110

Cys Cys Thr Cys Cys Ala Thr Cys Thr Cys Thr Thr Gly Cys Ala Gly
        115                 120                 125

Ala Thr Cys Thr Ala Gly Thr Cys Ala Gly Ala Gly Cys Cys Thr Thr
    130                 135                 140
```

-continued

Gly Thr Ala Cys Ala Cys Ala Gly Thr Ala Ala Thr Gly Gly Ala Ala
145 150 155 160

Ala Cys Ala Cys Cys Thr Ala Thr Thr Thr Ala Cys Ala Thr Thr Gly
165 170 175

Gly Thr Ala Cys Cys Thr Gly Cys Ala Gly Ala Ala Gly Cys Cys Ala
180 185 190

Gly Gly Cys Cys Ala Gly Thr Cys Thr Cys Cys Gly Ala Ala Gly Cys
195 200 205

Thr Cys Cys Thr Gly Ala Thr Cys Thr Cys Cys Ala Ala Ala Gly Thr
210 215 220

Thr Thr Cys Cys Ala Ala Cys Cys Gly Ala Thr Thr Thr Thr Cys Thr
225 230 235 240

Gly Gly Gly Gly Thr Cys Cys Cys Ala Gly Ala Cys Ala Gly Gly Thr
245 250 255

Thr Cys Ala Gly Thr Gly Gly Cys Ala Gly Thr Gly Gly Ala Thr Cys
260 265 270

Ala Gly Gly Gly Ala Cys Ala Gly Ala Thr Thr Thr Cys Ala Cys Ala
275 280 285

Cys Thr Cys Ala Ala Gly Ala Thr Cys Ala Gly Cys Ala Gly Ala Gly
290 295 300

Thr Gly Gly Ala Gly Gly Cys Thr Gly Ala Gly Gly Ala Thr Cys Thr
305 310 315 320

Gly Gly Gly Ala Gly Thr Thr Thr Ala Thr Thr Thr Cys Thr Gly Cys
325 330 335

Thr Cys Thr Cys Ala Ala Ala Gly Thr Ala Cys Ala Cys Ala Thr Gly
340 345 350

Thr Thr Cys Cys Gly Cys Thr Cys Ala Cys Gly Thr Thr Cys Gly Gly
355 360 365

Thr Gly Cys Thr Gly Gly Gly Ala Cys Cys Ala Ala Gly Cys Thr Gly
370 375 380

Gly Ala Gly Cys Thr Gly Ala Ala Ala Cys Gly Gly Gly Cys Thr Gly
385 390 395 400

Ala Thr Gly Cys Thr Gly Cys Ala Cys Cys Ala Ala Cys Thr Gly Thr
405 410 415

Ala Thr Cys Cys Ala Thr Cys Thr Thr Cys Cys Cys Ala Cys Cys Ala
420 425 430

Thr Cys Cys Ala Gly Thr Gly Ala Gly Cys Ala Gly Thr Thr Ala Ala
435 440 445

Cys Ala Thr Cys Thr Gly Gly Ala Gly Gly Thr Gly Cys Cys Thr Cys
450 455 460

Ala Gly Thr Cys Gly Thr Gly Thr Gly Cys Thr Thr Cys Thr Thr Gly
465 470 475 480

Ala Ala Cys Ala Ala Cys Thr Thr Cys Thr Ala Cys Cys Cys Cys Ala
485 490 495

Ala Ala Gly Ala Cys Ala Thr Cys Ala Ala Thr Gly Thr Cys Ala Ala
500 505 510

Gly Thr Gly Gly Ala Ala Gly Ala Thr Thr Gly Ala Thr Gly Gly Cys
515 520 525

Ala Gly Thr Gly Ala Ala Cys Gly Ala Cys Ala Ala Ala Ala Thr Gly
530 535 540

Gly Cys Gly Thr Cys Cys Thr Gly Ala Ala Cys Ala Gly Thr Thr Gly
545 550 555 560

```
Gly Ala Cys Thr Gly Ala Thr Cys Ala Gly Ala Cys Ala Gly Cys
                565                 570                 575
Ala Ala Ala Gly Ala Cys Ala Gly Cys Ala Cys Cys Thr Ala Cys Ala
            580                 585                 590
Gly Cys Ala Thr Gly Ala Gly Cys Ala Gly Cys Ala Cys Cys Cys Thr
            595                 600                 605
Cys Ala Cys Gly Thr Thr Gly Ala Cys Cys Ala Ala Gly Gly Ala Cys
            610                 615                 620
Gly Ala Gly Thr Ala Thr Gly Ala Ala Cys Gly Ala Cys Ala Thr Ala
        625                 630                 635                 640
Ala Cys Ala Gly Cys Thr Ala Thr Ala Cys Cys Thr Gly Thr Gly Ala
                645                 650                 655
Gly Gly Cys Cys Ala Cys Thr Cys Ala Cys Ala Ala Gly Ala Cys Ala
            660                 665                 670
Thr Cys Ala Ala Cys Thr Thr Cys Ala Cys Cys Cys Ala Thr Thr Gly
            675                 680                 685
Thr Cys Ala Ala Gly Ala Gly Cys Thr Thr Cys Ala Ala Cys Ala Gly
            690                 695                 700
Gly Ala Ala Thr Gly Ala Gly Thr Gly Thr Thr Ala Gly
705                 710                 715

<210> SEQ ID NO 11
<211> LENGTH: 238
<212> TYPE: PRT
<213> ORGANISM: Mus musculus

<400> SEQUENCE: 11

Met Lys Leu Pro Val Arg Leu Leu Val Leu Met Phe Trp Ile Pro Ala
1               5                   10                  15
Ser Ser Ser Asp Val Val Met Thr Gln Thr Pro Leu Ser Leu Pro Val
                20                  25                  30
Ser Leu Gly Asp Gln Ala Ser Ile Ser Cys Arg Ser Ser Gln Ser Leu
            35                  40                  45
Val His Ser Asn Gly Asn Thr Tyr Leu His Trp Tyr Leu Gln Lys Pro
        50                  55                  60
Gly Gln Ser Pro Lys Leu Leu Ile Ser Lys Val Ser Asn Arg Phe Ser
65                  70                  75                  80
Gly Val Pro Asp Arg Phe Ser Gly Ser Gly Ser Gly Thr Asp Phe Thr
                85                  90                  95
Leu Lys Ile Ser Arg Val Glu Ala Glu Asp Leu Gly Val Tyr Phe Cys
                100                 105                 110
Ser Gln Ser Thr His Val Pro Leu Thr Phe Gly Ala Gly Thr Lys Leu
            115                 120                 125
Glu Leu Lys Arg Ala Asp Ala Ala Pro Thr Val Ser Ile Phe Pro Pro
        130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
            180                 185                 190
Lys Asp Ser Thr Tyr Ser Met Ser Ser Thr Leu Thr Leu Thr Lys Asp
        195                 200                 205
Glu Tyr Glu Arg His Asn Ser Tyr Thr Cys Glu Ala Thr His Lys Thr
    210                 215                 220
```

Ser Thr Ser Pro Ile Val Lys Ser Phe Asn Arg Asn Glu Cys
225                 230                 235

<210> SEQ ID NO 12
<211> LENGTH: 112
<212> TYPE: PRT
<213> ORGANISM: Mus musculus

<400> SEQUENCE: 12

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 13
<211> LENGTH: 11
<212> TYPE: PRT
<213> ORGANISM: Mus musculus

<400> SEQUENCE: 13

Gln Ser Leu Val His Ser Asn Gly Asn Thr Tyr
1               5                   10

<210> SEQ ID NO 14
<211> LENGTH: 3
<212> TYPE: PRT
<213> ORGANISM: Mus musculus

<400> SEQUENCE: 14

Lys Val Ser
1

<210> SEQ ID NO 15
<211> LENGTH: 9
<212> TYPE: PRT
<213> ORGANISM: Mus musculus

<400> SEQUENCE: 15

Ser Gln Ser Thr His Val Pro Leu Thr
1               5

ANTIBODY COMPOSITIONS TARGETING NON-PHOSPHORYLATED ALPHA-SYNUCLEIN AGGREGATES

CROSS-REFERENCE TO RELATED APPLICATION

This application is a continuation-in-part of PCT/QA2021/050019, filed Sep. 17, 2021, which claims the benefit of U.S. Provisional Patent Application No. 63/079,767, filed Sep. 17, 2020, each of which is incorporated herein by reference in its entirety.

BACKGROUND

Parkinson's disease (PD) and dementia with Lewy bodies (DLB) are collectively known as Lewy body disease and are the second most common neurodegenerative disorder after Alzheimer's disease (AD). The neuropathological hallmark of Lewy body disease is the intracellular aggregation of the protein alpha-synuclein (α-syn) into spherical cytoplasmic inclusions termed Lewy bodies, but aggregates are also observed in neuronal processes as Lewy neurites.

Alpha-synuclein is thought to play a central role in the pathobiology of Lewy body disease. Single point mutations and genetic modifications affecting α-syn expression, through duplications, triplications, or polymorphisms in its promoter, have been linked to both idiopathic and familial forms of PD as well as Lewy body disease. Nevertheless, neuropathological studies utilizing pan-α-syn antibodies, recognizing both physiological and pathological forms of the protein, do not consistently report a relationship between the load of Lewy body pathology and clinical disease severity. The effort in reconciling the apparent importance of α-syn in Lewy body disease, with the difficulty relating Lewy body burdens in the brain to phenotypic severity, has stimulated the search for particularly disease-relevant forms of α-syn. This protein undergoes various post-translational modifications (PTMs), including acetylation, nitration, ubiquitination and glycosylation. Phosphorylation at serine 129 (pS129) increases from approximately 4% under physiological conditions to 90% in Lewy body disease, making this modification a focus as a potential driver of the disease process.

SUMMARY

There is a need for biomarkers for Lewy body dementias, including Parkinson's disease (PD) and dementia with Lewy bodies (DLB), and reagents for their detection. Aggregated non-phosphorylated α-synuclein is a biomarker for the Lewy body dementias, especially their early stages. Disclosed herein are an antibody that binds aggregated non-phosphorylated α-synuclein, and methods for generating and using such antibodies.

One aspect is a monoclonal antibody that specifically binds aggregated, non-phosphorylated α-synuclein. In some embodiments, the antibody does not bind to phosphorylated α-synuclein. In some embodiments, the antibody does not to non-phosphorylated α-synuclein monomers. In some embodiments, the epitope recognized by the antibody includes the serine residue at position 129 of α-synuclein, a site at which α-synuclein can become phosphorylated. In some embodiments, the antibody recognizes, and can be induced by, a peptide comprising or consisting of amino acid residues 125-133 of α-synuclein (SEQ ID NO:1), namely YEMPSEEGY (SEQ ID NO: 2), for example, the peptide CYEMPSEEGY (SEQ ID NO: 3). Such antibodies can be referred to as means for specifically binding to aggregated, non-phosphorylated α-synuclein. Some embodiments are compositions comprising a monoclonal antibody that binds aggregated, non-phosphorylated α-synuclein and a carrier, solvent, buffer, or other excipient. In some embodiments, the antibody is the monoclonal antibody produced by the hybridoma 4B1 which has been deposited with the American Type Culture Collection (ATCC), Patent Deposit Number PTA-127017. In some embodiments, the antibody has high affinity to an epitope comprising the amino acid 125-133 region with non-phosphorylated Ser at position 129 of α-synuclein. In some embodiments, the epitope is linear. In some embodiments, the antibody has high affinity for α-synuclein aggregates but low affinity for α-synuclein monomers.

One aspect is a method of generating a monoclonal antibody that binds aggregated, non-phosphorylated α-synuclein comprising immunizing a mouse with a peptide comprising or consisting of amino acid residues 125-133 of α-synuclein, namely YEMPSEEGY (SEQ ID NO: 2), for example, the peptide CYEMPSEEGY (SEQ ID NO: 3). The peptide consisting of the sequence CYEMPSEEGY (SEQ ID NO: 3) may be referred to as means for inducing antibodies recognizing aggregated, non-phosphorylated α-synuclein. In some embodiments, the immunizing peptide is conjugated to a carrier protein, for example, keyhole limpet hemocyanin. In some embodiments, the method further comprises standard procedures for generating and selecting hybridomas, as are known to those of skill in the art. Hybridomas are produced by hybridoma technology where antibody producing B-cells are fused with myeloma cells followed by selection and screening. Monoclonal antibodies can also be produced using other technologies including phage display and single B cell antibody technology. Other embodiments are a monoclonal antibody generated by any of these methods.

One aspect is a hybridoma generated by a method comprising immunizing a mouse with a peptide comprising amino acid residues 125-133 of α-synuclein, namely YEMPSEEGY (SEQ ID NO: 2). In some embodiments, the peptide comprising amino acid residues 125-133 of α-synuclein is CYEMPSEEGY (SEQ ID NO: 3).

One aspect is a hybridoma that produces an antibody that binds aggregated, non-phosphorylated α-synuclein comprising immunizing a mouse with a peptide comprising amino acid residues 125-133 of α-synuclein, namely YEMPSEEGY (SEQ ID NO: 2). In some embodiments, the peptide comprising amino acid residues 125-133 of α-synuclein is CYEMPSEEGY (SEQ ID NO: 3).

One aspect is a hybridoma that produces an antibody that specifically binds aggregated, non-phosphorylated α-synuclein. In some embodiments, the hybridoma is 4B1, ATCC Patent Deposit Number PTA-127017. Some embodiments are antibodies having the variable region amino acid sequences or CDR amino acid sequences of the monoclonal antibody produced by the 4B1 hybridoma (ATCC Patent Deposit Number PTA-127017). Some embodiments are nucleic acids (DNA or RNA) comprising encoding sequences for the variable region amino acid sequences or CDR amino acid sequences of the monoclonal antibody produced by the 4B1 hybridoma (ATCC Patent Deposit Number PTA-127017).

One aspect is a method of making a monoclonal antibody that binds aggregated, non-phosphorylated α-synuclein comprising culturing a hybridoma that secretes the antibody and collecting the culture supernatant. Some embodiments further comprise purifying the antibody from the culture supernatant. In some embodiments, the hybridoma is 4B1, ATCC Patent Deposit Number PTA-127017. Other embodiments are a monoclonal antibody made by any of these methods.

One aspect comprises nucleic acid molecules encoding a monoclonal antibody, whole or fragment thereof, that specifically binds aggregated, non-phosphorylated α-synuclein. In some embodiments, the nucleic acids encode a heavy chain variable domain with heavy chain complementarity determining regions (HCDRs) having the amino acid sequences of SEQ ID NOs: 7-9 and light chain variable domain with light chain complementarity determining regions (LCDRs) having the amino acid sequences of SEQ ID NOS: 13-15. In some embodiments, the nucleic acids encode a heavy chain variable domain having the amino acid sequence of SEQ ID NO: 6 and a light chain variable domain having the amino acid sequence of SEQ ID NO: 12. In some embodiments, the nucleic acid molecules encode a heavy chain having the amino acid sequence of SEQ ID NO: 5 and a light chain having the amino acid sequence of SEQ ID NO: 11. In some embodiments, the encoding nucleic acid molecules are isolated, that is, not associated with any sort of organism or cell. In some embodiments, the nucleic acid molecules are contained within a host cell capable of replicating the nucleic acids, for example, by being integrated into a plasmid in a bacterial cell. In some embodiments, the nucleic acid molecules are contained within a host cell capable of expressing the antibody from the nucleic acid molecules. In some embodiments, a nucleic acid molecule encoding the monoclonal antibody is cDNA. In some instances, the encoding cDNA is integrated into the genome of a host cell. In some instances, the encoding cDNA is episomal. In some embodiments, the nucleic acid molecules encoding the monoclonal antibody is mRNA. In some instances, the uridine residues in the mRNA are substituted with a modified nucleoside, for example, pseudouridine. In some instances, an isolated mRNA is formulated in a lipid nanoparticle. In some embodiments, the nucleic acid sequence encoding the light chain and the heavy chain are contained within a single nucleic acid molecule. In some embodiments, the nucleic acid sequence encoding the light chain and the heavy chain are contained within a separate nucleic acid molecules.

With respect to the above aspects, in some embodiments, the monoclonal antibody that specifically binds aggregated, non-phosphorylated α-synuclein comprises a heavy chain variable domain with heavy chain complementarity determining regions (CDRs) having the amino acid sequences of SEQ ID NOs: 7-9 and light chain variable domain with light chain CDRs having the amino acid sequences of SEQ ID NOS: 13-15. In some embodiments, the monoclonal antibody that specifically binds aggregated, non-phosphorylated α-synuclein comprises a heavy chain variable domain having the amino acid sequence of SEQ ID NO; 6 and a light chain variable domain having the amino acid sequence of SEQ ID NO: 12. In some embodiments, the monoclonal antibody that specifically binds aggregated, non-phosphorylated α-synuclein comprises a heavy chain having the amino acid sequence of SEQ ID NO; 5 and a light chain having the amino acid sequence of SEQ ID NO: 11. These embodiments constitute means for binding WT-α-syn.

BRIEF DESCRIPTION OF DRAWINGS

FIGS. 1A-E depict the effect of pS129 on α-syn aggregation and its ability to seed the polymerization/aggregation of α-syn. FIG. 1A. Monomeric α-syn was incubated in the presence of various percentages (0, 5, 20, 50 and 100%) of monomeric pS129-α-syn (final concentration 100 µM) for 20 days at 37° C. with continuous shaking. Fibril formation was evaluated by Th—S fluorescence. The assay was performed in triplicates, and the means±standard deviations are shown. FIGS. 1B and 1C. Monomeric WT-α-syn (100 µM) was incubated alone, with 2 µM (FIG. 1B) or 0.1 µM (FIG. 1C) (final concentration) of pS129 seeds or WT seeds for 48 hours. FIGS. 1D and 1E. Samples of monomeric pS129-α-syn (100 µM) were incubated alone or with 2 µM (FIG. 1D) or 0.1 µM (FIG. 1E) (final concentration) of pS129 seeds or WT seeds for 48 hours. Fibril formation was evaluated by Th—S fluorescence. The assay was performed in triplicates, and the means±standard deviations are shown. (* $p<0.05$, ** $p<0.01$).

FIG. 4A. Treatment with α-syn seeds in a concentration of 100 nM for 4 days. Representative images of cells under the different treatments. DAPI was used for nuclear staining. Scale bar=10 µm. FIG. 4B. Quantification of the percentage of cells with inclusions (>200 cells counted per condition, 4 independent experiments; mean±SD) revealed that pS129-α-syn is less potent than WT-α-syn in seeding aggregation, #: comparison WT seeds to pS129-α-syn seeds (**$p<0.01$).

FIG. 5A. Representative images of aggregates in the DG at various time points post injection of PFF, stained for WT-α-syn with 4B1 and pS129-α-syn. Arrowheads indicate the different types of aggregates; small LNs (rightward pointing arrowheads in the 3 dpi panel, top and bottom arrowhead in the 5 dpi panel, downward pointing arrowhead in the 10 dpi panel, and upper right-ward pointing arrow head in 14 dpi panel), intermediate LNs (left-ward point arrowhead in 3 dpi panel, central two arrowheads in 5 dpi panel, lower two arrowheads in 7 dpi panel, upper rightward pointing arrowheads in 10 dpi panel and bottom arrowhead in 14 dpi panel), large LNs (upper arrowhead in 7 dpi panel, lower left arrowhead in 10 dpi panes, and downward and left-ward pointing arrowheads in 14 dpi panel) and cell body inclusions (lower right arrowhead in 10 dpi panel). Scale bars=20 µm. FIG. 5B. Relative MFI of WT- vs. pS129-α-syn staining in the total population of aggregates. FIG. 5C. Area proportion of WT-α-syn in the total population of aggregates. FIG. 5D. Relative MFI of WT- vs. pS129-α-syn staining in DG aggregates. FIG. 5E. Area proportion of WT-α-syn in DG aggregates. FIG. 5F. Relative MFI of WT- vs. pS129-α-syn staining in each type of aggregate (small LNs, intermediate LNs, large LNs and cell body inclusions), all time points collapsed. FIG. 5G. Area proportion of WT-α-syn in each type of aggregate, all time points collapsed. FIG. 5H. Illustration of the changes in size and density of WT-α-syn inside aggregates, depending on their morphology. All graphs are displayed as mean±SEM, normalized to the first bar (* $p<0.05$,  $p<0.01$, * $p<0.001$, **** $p<0.0001$).

FIGS. 6A-B displays immunofluorescence analysis on brain sections from mice injected with recombinant α-syn PFFs. FIG. 6A. Free-floating cryostat-cut coronal sections (30 µm) 1, 2, and 4 weeks post stereotaxic injections, covering the whole nigrostriatal axis were stained with antibodies against pS129-α-syn, WT-α-syn (4B1) and DAT. FIG. 6B. To validate whether pS129-α-syn accumulations were proteinase K (PK) resistant, sections were incubated with PK.

FIG. 7A. Sections were obtained from the amygdala of a Parkinson's disease dementia (PDD; i-iv) and DLB (v-viii) case and stained with pS129 and 4B1 on consecutive sections. Sections were imaged at precisely the same location on both slides. Scale bars=200 µm (i, ii, v, vi), 50 µm (iii, iv, vii, viii). FIG. 7B. WT-α-syn expression in the amygdala was evaluated with disease duration across all cases, showing a strong inverse relationship. FIG. 7C. Amygdala sections from DLB and PDD cases were double-labelled with pS129 and 4B1 antibodies for immunofluorescent analysis. (Images displayed are amygdala sections from DLB).

FIG. 8A. Characterization of monomeric and aggregated α-syn by immunoblotting. FIG. 8B. Th—S fluorescence readings of the monomeric and aggregated α-syn samples. FIG. 8C. Immunoblotting for α-syn samples incubated with PLK2 at different time points. Phosphorylation at S129 was detected by pS129-α-syn-specific antibody. Total α-syn was detected by anti-α-syn (211) antibody. FIG. 8D. Fibril content estimation in the pS129-α-syn seeds, WT-α-syn seeds and aggregated α-syn by Th—S fluorescence. The assay was performed in triplicates and, the means±standard deviations are shown. FIG. 8E. Electron microscopy images of negatively stained samples of pS129-α-syn seeds, WT-α-syn seeds and aggregated α-syn (100 µM). Scale bar 500 nm.

FIG. 10A. Immunoblotting of cell lysates for total α-syn detection using the mouse monoclonal anti-α-syn (211) antibody and β-actin as loading control. FIG. 10B. Quantification of α-syn expression levels by densitometric analysis using ImageJ software. FIG. 10C-E. The viability of BE(2)-M17 WT cells was estimated by the MTT assay. The results are expressed as the percentage of the control average (i.e., untreated cells).. BE(2)-M17 WT cells were treated with different concentrations of α-syn pure fibrils (FIG. 10C), pure seeds (FIG. 10D), or monomeric WT-α-syn (FIG. 10E). The assay was performed in triplicates and the means±standard deviation are shown. (*, $p<0.05$).

FIGS. 12A-B depict the purity and specificity of 4B1 towards WT-α-syn aggregates. FIG. 12A, panel i. 50 ng of recombinant WT-, pS129-, or S129A-α-syn was loaded on 15% SDS gels and transferred to nitrocellulose membranes for western blotting. FIG. 12A, panel ii. Filter retardation assessment for 4B1 reactivity towards α-syn. F11 detects α- or β-syn, whereas the antibody E20 detects γ-syn. Filter retardation analysis of 4B1 reactivity towards human (H-α-syn) or mouse (M-α-syn). FIG. 12B, panel i. Analysis of filter retardation using monomeric-(M) or fibrillar-(F) α-syn coated on nitrocellulose membranes and detected with 4B1, Syn-1, and Syn-02. Reactivity of 4B1 towards different α-syn aggregates including fibrils, ONE- or HNE. FIG. 12B, panel ii. 4B1 pre-incubated with monomers or ONE-oligomers and tested against pre-coated monomeric α-syn in inhibition ELISA. FIG. 12B, panel iii. Sandwich-ELISA showing the reactivity of 4B1 towards monomers or different α-syn aggregates.

DESCRIPTION

Figure 2A:
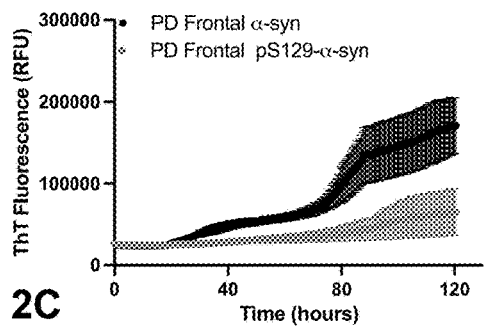
FIGS. 2A-G depict the effect of pS129 on nucleation-dependent polymerization by RT-QuIC assay. The assay was performed using recombinant monomeric WT-α-syn or p-S129-α-syn used as substrates in FIGS. 2A-D on samples from PD and DLB frontal and temporal regions. When used as a substrate, monomeric WT-α-syn showed higher seeding propensity compared to p-S129-α-syn as shown by shortest lag-phase (FIG. 2E), highest aggregation rate (FIG. 2F), and highest FMAX value reached at end of the reaction (FIG. 2G). The amplification curves show the mean fluorescence in each time point with standard error as shaded area. One-way ANOVA with Tukey's multiple comparison testing was used for statistical comparisons. (*, $p<0.001$; , $p<0.001$; *, $p<0.01$; $p<0.05$).
Figure 2B:
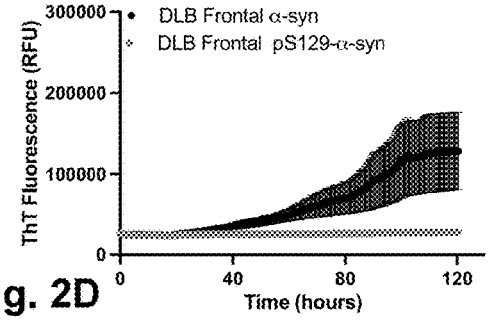
Figure 2C:
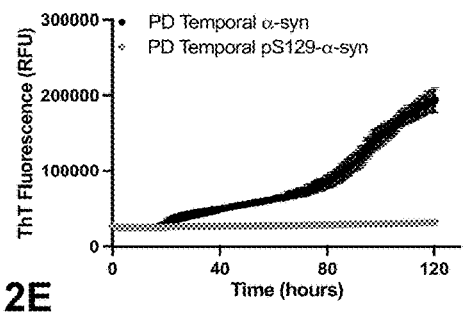
Figure 2D:
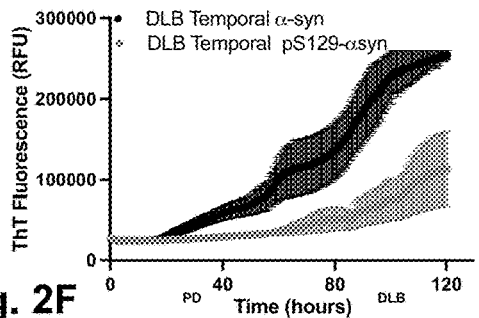
Figure 2E:
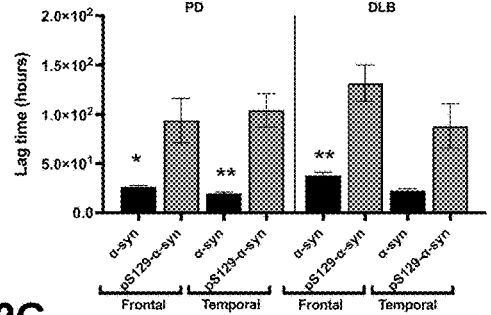
Figure 2F:
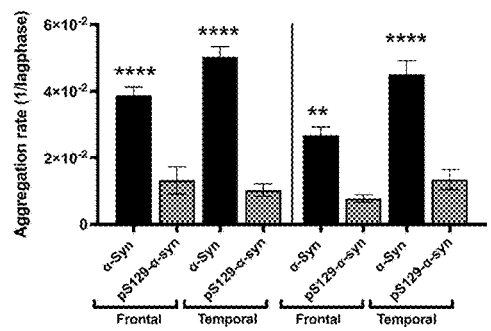
Figure 2G:
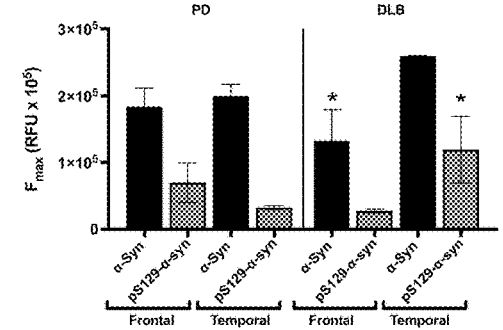

Parkinson's disease (PD) and dementia with Lewy bodies (DLB) are commonly called α-synucleinopathies and idiopathic and familial forms of these diseases have been linked to abnormal expression of α-synuclein (α-syn). Nevertheless, neuropathological studies utilizing pan-α-syn antibodies, recognizing both physiological and pathological forms of the protein, do not consistently report a relationship between the load of Lewy body pathology and clinical disease severity. However, multiple forms or α-syn arising from post-translational modifications exist. These include acetylation, nitration, ubiquitination, glycosylation, and phosphorylation. Notably, phosphorylation at serine 129 (pS129) increases from approximately 4% under normal physiology to 90% in Lewy body disease, indicating that this form of α-syn may be important in the disease process.

Some studies have associated the pS129 modification with intracellular aggregate formation leading to cell death mediated by the unfolded protein response. Rodent models have suggested that the pS129 modification exacerbates the rate of pathological protein aggregation and deposition, with subsequent negative effects on neuronal functioning. Yet other studies in animal and cellular model systems report a potentially neuroprotective function of phosphorylation. Still other studies have found the pS129 modification neither increases nor diminishes cellular toxicity and/or α-syn aggregation. Nonetheless, antibodies specific for pS129 are widely used as a putative disease relevant marker. Such studies often employ pS129-α-syn as a marker of the abundance of protein inclusions to stage disease severity and evaluate the relationship between its abundance and important clinical or pathological variables, such as disease duration, phenotypic severity or cell loss, and correlate the abundance of pS129 throughout the brain with disease severity. However, it has remained uncertain whether phosphorylation precedes protein aggregation or occurs secondarily to deposition of non-phosphorylated α-syn, or whether pS129 is a driver of pathogenicity or merely a useful marker of the neurodegenerative process. We disclose herein a monoclonal antibody specific for WT-α-syn (that is, the form that remains unphosphorylated at serine 129), useful in addressing these and other questions related to the generation of α-syn aggregates and the role of the phosphorylated and unphosphorylated forms of α-syn in aggregation propensity and cytotoxicity.

As used herein non-phosphorylated α-synuclein means α-synuclein in which the serine residue at position 129 is not phosphorylated.

The term "antibody" is herein used in the broadest sense and encompasses various antibody structures including, but not limited to, monoclonal antibodies, polyclonal antibodies, multispecific antibodies (e.g., bispecific antibodies), and antibody fragments so long as they exhibit the desired antigen-binding activity. An antibody broadly refers to any immunoglobulin (Ig) molecule comprised of heavy (H) chains and light (L) chains, or any functional fragment, mutant, variant, or derivation thereof, which retains the essential epitope-binding features of an Ig molecule. Such mutant, variant, or derivative antibody formats are known in the art, non-limiting embodiments of which are discussed below. An antibody is said to be "capable of binding" a molecule if it is capable of specifically reacting with the molecule. As used herein, the term "fragment", when referring to an antibody should be read to mean an antigen-binding fragment. Various embodiments encompass both whole antibodies and antibody fragments, while other embodiments are limited to only whole antibodies or only antibody fragments or only one or more particular types of antibody fragment.

The term "monoclonal antibody," as used herein, refers to an antibody obtained from identical immune cells that are clones of a unique parent cell and expressed from a particular, single encoding sequence (neglecting such variation as may arise in the expression system or cell). Typically, monoclonal antibodies are monospecific in that all of the antigen binding sites contain the same complementarity determining regions (CDRs) and thus bind to the same epitope. The modifier "monoclonal" indicates the character of the antibody as being obtained from a clonal source and is not to be construed as requiring production of the antibody by any particular method. Thus the term encompasses antibodies obtained through traditional hybridoma technology, but also those obtained by phage display and other molecular cloning technologies.

The term "variable region" or "variable domain" refers to the domain of an antibody heavy or light chain that is involved in binding the antibody to antigen, such as that of the monoclonal antibody produced by the 4B1 hybridoma (ATCC Patent Deposit Number PTA-127017). The variable domains of the heavy chain and light chain (VH and VL, respectively) of a native antibody generally have similar structures, with each domain comprising four conserved framework regions (FRs) and three hypervariable regions termed complementarity determining regions (CDRs). (See, e.g., Kindt et al. Kuby Immunology, 6th ed., W. H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively.

An "antigen-binding portion" or "antigen-binding fragment" of an antibody (or simply "antibody portion" or "antibody fragment") refers to a molecule other than an intact or whole antibody that comprises a portion of an intact antibody that binds the antigen to which the intact antibody binds (e.g., one or more fragments of an antibody that retain the ability to specifically bind to an antigen). Examples of antibody fragments include, but are not limited to, Fv, Fab, Fab', Fab'-SH, F(ab')$_2$, diabodies, linear antibodies, single-chain antibody molecules (e.g. scFv), heavy chain only antibodies (HCAb), and multispecific antibodies formed from antibody fragments. Papain digestion of intact antibodies produces two identical antigen-binding fragments, called "Fab" fragments, each with a single antigen-binding site, and a residual "Fc" fragment, whose name reflects its ability to crystallize readily. Pepsin treatment yields an F(ab')₂ fragment that has two antigen-combining sites and is still capable of cross-linking antigen. However these terms may also be applied to genetically encoded fragments of the same or similar nature, in addition to those fragments produced by proteolytic digestion. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding portion" of an antibody. Other forms of single chain antibodies, such as diabodies are also encompassed.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent and/or bispecific. Diabodies are described more fully in, for example, EP 404,097; WO 1993/01161; Hudson et al., Nat. Med. 9: 129-134 (2003); and Hollinger et al., Proc. Natl. Acad. Sci. USA 90: 6444-6448 (1993). Triabodies and tetrabodies are also described in Hudson et al., Nat. Med. 9: 129-134 (2003).

The "Fab" fragment contains the heavy- and light-chain variable domains and also contains the constant domain of the light chain and the first constant domain (CH1) of the heavy chain, such as those of the monoclonal antibody produced by the 4B1 hybridoma (ATCC Patent Deposit Number PTA-127017). Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')₂ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions.

"Framework" or "FR" refers to variable domain residues other than complementarity determining region (CDR) residues, such as those of the monoclonal antibody produced by the 4B1 hybridoma (ATCC Patent Deposit Number PTA-127017). The FR of a variable domain generally consists of four FR domains: FR1, FR2, FR3, and FR4. Accordingly, the CDR and FR sequences generally appear in the following sequence in either VH or VL sequences: FR1-CD1-FR2-CDR2-FR3-CDR3-FR4.

The terms "full length antibody," "intact antibody," and "whole antibody" are used herein interchangeably to refer to an antibody having a structure substantially similar to a native antibody structure or having heavy chains that contain an Fc region as defined herein.

"Fv" refers to the minimum antibody fragment which contains a complete antigen-binding site, such as that of the monoclonal antibody produced by the 4B1 hybridoma (ATCC Patent Deposit Number PTA-127017). In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "class" of an antibody refers to the type of constant domain or constant region possessed by its heavy chain. There are five major classes of antibodies in humans: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. In some embodiments, recombinant technology can be used to change the isotype of an antibody.

The term "epitope" or "antigenic determinant" includes any protein or polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules. Different epitopes may occupy the same or topological region of an antigen. With respect to α-syn, antibodies that bind WT-α-syn (unphosphoylated at S129), pS129-α-syn, or that bind both forms of α-syn, each bind distinct epitopes.

The present disclosure also encompasses functional equivalents of the antibodies described in this specification. Functional equivalents have binding characteristics that are comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424, which are incorporated in their respective entireties by reference. Functional equivalents include polypeptides with amino acid sequences substantially the same as the amino acid sequence of the variable or hypervariable regions of the antibodies disclosed herein, such as the monoclonal antibody produced by the 4B1 hybridoma (ATCC Patent Deposit Number PTA-127017). "Substantially the same" as applied to an amino acid sequence is defined herein as a sequence with at least about 90%, and more preferably at least about 95% sequence identity to another amino acid sequence, as determined by the FASTA search method in accordance with Pearson and Lipman, Proc. Natl. Acad. Sci. USA 85, 2444-2448 (1988) and retaining binding specificity to the target antigen. Thus some embodiments are functionally equivalent to, or substantially similar to, the amino acid sequence of the monoclonal antibody produced by the 4B1 hybridoma (ATCC Patent Deposit Number PTA-127017).

Some embodiments are antibodies comprising an antigen binding portion that is a functional equivalent of the antigen binding portion of the herein disclosed antibodies. Such antibodies are encompassed by the term "antibody means for binding WT-α-syn" or simply "means for binding WT-α-syn".

One aspect is a monoclonal antibody that specifically binds aggregated, non-phosphorylated α-synuclein (an anti-WT-α-syn antibody). In some embodiments, the antibody does not bind to phosphorylated α-synuclein. In some embodiments, the antibody does not bind to non-phosphorylated α-synuclein monomers. In some embodiments, the epitope recognized includes the serine residue at position 129 of α-synuclein, a site at which α-synuclein becomes phosphorylated. In some embodiments, the antibody recognizes, and can be induced by, a peptide comprising or consisting of amino acid residues 125-133 of α-synuclein (SEQ ID NO:1), namely YEMPSEEGY (SEQ ID NO: 2), for example, the peptide CYEMPSEEGY (SEQ ID NO: 3). Such antibodies can be referred to as means for specifically binding to aggregated, non-phosphorylated α-synuclein. Some embodiments are compositions comprising a monoclonal antibody that binds aggregated, non-phosphorylated α-synuclein and a carrier, solvent, buffer, or other excipient. In some embodiments, the antibody is the monoclonal antibody produced by the hybridoma 4B1, ATCC Patent Deposit Number PTA-127017.

In various embodiments, the monoclonal antibody that specifically binds aggregated, non-phosphorylated α-synuclein does not bind one or more of pS129-α-syn, S129A-α-syn (in which serine is replaced with alanine), β-synuclein, or γ-synuclein. In various embodiments binding specificity is determined by western blot, ELISA, slot blot, or any combination thereof. In some embodiments, the antibody has high affinity to an epitope comprising amino acids 125-133 of α-synuclein with non-phosphorylated Ser at position 129 of α-synuclein. In some embodiments, the epitope is linear. In some embodiments, the antibody has high affinity for α-synuclein aggregates but low affinity for α-synuclein monomers. In a facet of these embodiments, the α-synuclein aggregates are protofibrils or soluble oligomers of α-synuclein and the antibody can have high affinity for the protofibrils, the soluble oligomers, or both. In other facets of these embodiments, the α-synuclein aggregates are α-synuclein fibrils.

One aspect is a method of generating an antibody that binds, or antiserum specific for, aggregated, non-phosphorylated α-synuclein comprising immunizing a mouse or other laboratory animal (for example, a rat, a hamster, or a rabbit) or an agricultural animal (for example, a goat, a sheep, or a horse) with a peptide comprising of amino acid residues 125-133 of α-synuclein (SEQ ID NO:1), namely YEMPSEEGY (SEQ ID NO: 2), for example, the peptide CYEMPSEEGY (SEQ ID NO: 3) may be referred to as means for inducing antibodies recognizing aggregated, non-phosphorylated α-synuclein. In some embodiments, the immunizing peptide is conjugated to a carrier protein, for example, keyhole limpet hemocyanin, Concho/epas concholepas hemocyanin, bovine serum albumin, ovalbumin, or diphtheria or tetanus toxoid. In some embodiments, the antibody is a monoclonal antibody. In some embodiments, the method further comprises standard procedures for generating and selecting hybridomas, as are known to those of skill in the art. Some embodiments are a monoclonal antibody generated by any of these methods.

One aspect is an antibody that binds, or antiserum specific for, aggregated, non-phosphorylated α-synuclein made by a process comprising immunizing a mouse with a peptide comprising or consisting of amino acid residues 125-133 of α-synuclein (SEQ ID NO: 1), namely YEMPSEEGY (SEQ ID NO: 2), for example, the peptide CYEMPSEEGY (SEQ ID NO: 3). Some embodiments further comprise applying hybridoma technology or molecular cloning technology to obtain a monoclonal antibody.

Some embodiments are a monoclonal antibody generated by (or made by a process comprising) immunizing a laboratory animal with means for inducing antibodies recognizing aggregated, non-phosphorylated α-synuclein. In some embodiments, the laboratory animal is a mouse. In some embodiments, the means for inducing antibodies recognizing aggregated, non-phosphorylated α-synuclein are conjugated to a carrier protein. In some embodiments, the carrier protein is keyhole limpet hemocyanin. In some embodiments, the means for inducing antibodies recognizing aggregated, non-phosphorylated α-synuclein is the peptide CYEMPSEEGY (SEQ ID NO:3). Some embodiments further comprise screening hybridomas for reactivity of the antibody against recombinant WT-α-syn. Some embodiments further comprise a counter-screens for a lack of reactivity of the antibody against one or more of pS129-α-syn, S129A-α-syn (in which serine is replaced with alanine), β-synuclein, or γ-synuclein. In some embodiments, the screening (or counter-screening) comprises an ELISA. In some embodiments, the screening (or counter-screening) comprises filter retardation assay analysis.

With respect to any of the antibody aspects, some embodiments are pharmaceutical compositions comprising the antibody. A pharmaceutical composition is one intended and suitable for the treatment of disease in humans. That is, it provides overall beneficial effect and does not contain amounts of ingredients or contaminants that cause toxic or other undesirable effects unrelated to the provision of the beneficial effect. A pharmaceutical composition will contain one or more active agents and may further contain solvents, buffers, diluents, carriers, and other excipients to aid the administration, solubility, absorption or bioavailability, and or stability, etc. of the active agent(s) or overall composition. A "pharmaceutically acceptable carrier, diluent, or excipient" is a medium generally accepted in the art for the delivery of biologically active agents to mammals, e.g., humans. The compounds of the present invention can be formulated as pharmaceutical compositions using a pharmaceutically acceptable carrier, diluent, or excipient and administered by a variety of routes. In particular embodiments, such compositions are for oral or intravenous administration. Such pharmaceutical compositions and processes for preparing them are well known in the art. See, e.g., REMINGTON: THE SCIENCE AND PRACTICE OF PHARMACY (A. Gennaro, et al., eds., 19.sup.th ed., Mack Publishing Co., 1995).

Aspects of the present specification provide, in part, administering a therapeutically or prophylactically effective amount of an anti-α-synuclein antibody or a pharmaceutical composition thereof. As used herein, the term "therapeutically effective amount" is synonymous with "therapeutically effective dose" and when used in reference to treating a neurodegenerative disorder associated with α-synuclein, such as Parkinson's disease, dementia with Lewy bodies, Alzheimer's disease, or multiple system atrophy, means at least the minimum dose of a compound or composition disclosed herein necessary to achieve the desired therapeutic or prophylactic effect. In some embodiments, it refers to an amount sufficient to prevent, slow, or halt the neurodegenerative process. In some embodiments, it includes a dose sufficient to reduce a symptom associated with the neurodegenerative disease. An effective dosage or amount of an anti-α-synuclein antibody or a composition thereof can readily be determined by the person of ordinary skill in the art considering all criteria (for example, the rate of excretion of the compound or composition used, the pharmacodynamics of the compound or composition used, the nature of the other compounds to be included in the composition, the particular route of administration, the particular characteristics, history and risk factors of the individual, such as, e.g., age, weight, general health and the like, the response of the individual to the treatment, or any combination thereof) and utilizing his best judgment on the individual's behalf.

The terms "treatment," "treating", etc., refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. Various embodiments may specifically include or exclude one or more of these modes of treatment. The herein disclosed anti-α-synuclein antibodies may be used as medicaments for the treatment of α-synuclein-associated neurodegenerative disorders. Further embodiments are methods of treating α-synuclein-associated neurodegenerative disorders comprising administering an anti-α-synuclein antibody to a subject in need thereof. In some embodiments, the α-synuclein-associated neurodegenerative disorder is Parkinson's disease, dementia with Lewy bodies, Alzheimer's disease, or multiple system atrophy. In some embodiments, the subject in need thereof is a human. In some embodiments, the antibody may be administered directly to the site of α-synuclein aggregate deposit, e.g. a Lewy body, such as by injection into a blood vessel supplying the brain or into the brain itself.

As formation of aggregates of unphosphorylated α-synuclein appear to precede the inclusion of phosphorylated α-synuclein in the aggregates, use of an antibody with specificity for the unphosphorylated form can allow earlier or more effective intervention to slow, halt, or reverse progression of the neurodegenerative disease. Thus, some methods of treating α-synuclein-associated neurodegenerative disorder comprise managing or delaying the onset of the condition, or reducing the risk of developing or worsening of the condition. In various instances, the α-synuclein-associated neurodegenerative disorder is Parkinson's disease, dementia with Lewy bodies, Alzheimer's disease, or multiple system atrophy.

Further embodiments, comprise altering the treatment regime of the individual based on the comparison of the detected levels of antibody-α-synuclein complexes with the reference level, as described below. The treatment regime can be altered by changing the drugs administered to treat the disease and/or changing the frequency and/or dose of the drug administered, depending on the progression of the disease. An increased level of the complex compared to a base line level will typically indicate that the individual has or is in the process of developing an α-synuclein pathology. The base line level will typically be calculated from a sample from an individual known not to have an α-synuclein pathology (a "normal individual") or from an earlier test of a sample taken from the same individual being tested.

One aspect is a method of making a monoclonal antibody that binds aggregated, non-phosphorylated α-synuclein comprising culturing a hybridoma that secretes the antibody and collecting the culture supernatant. Some embodiments further comprise purifying the antibody from the culture supernatant. The antibodies are suitably separated from the culture medium by conventional immunoglobulin purification procedures such as, for example, proteins G-Sepharose, protein A-Sepharose, hydroxyapatite chromatography, gel electrophoresis, dialysis, or affinity chromatography. Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt). In some embodiments, the hybridoma is 4B1, ATCC Patent Deposit Number PTA-127017. Further embodiments are a monoclonal antibody that binds aggregated, non-phosphorylated α-synuclein made by any of these method of making embodiments.

One aspect comprises nucleic acid molecules encoding a monoclonal antibody, whole or fragment thereof, that specifically binds aggregated, non-phosphorylated α-synuclein. In some embodiments, the nucleic acids encode a heavy chain variable domain with HCDR1-HCDR3 having the amino acid sequences of SEQ ID NOs: 7-9, respectively, and light chain variable domain with LCDR1-LCDR3 having the amino acid sequences of SEQ ID NOS: 13-15, respectively. In some embodiments, the nucleic acids encode a heavy chain variable domain having the amino acid sequence of SEQ ID NO; 6 and a light chain variable domain having the amino acid sequence of SEQ ID NO: 12. In some embodiments, the nucleic acid molecules encode a heavy chain having the amino acid sequence of SEQ ID NO; 5 and a light chain having the amino acid sequence of SEQ ID NO: 11. In some embodiments, the encoding nucleic acid molecules are isolated, that is, not associated with any sort of organism or cell. In some embodiments, the nucleic acid molecules are contained within a host cell capable of replicating the nucleic acids, for example, by being integrated into a plasmid in a bacterial cell. In some embodiments, the nucleic acid molecules are contained within a host cell capable of expressing the antibody from the nucleic acid molecules. In some embodiments, a nucleic acid molecule encoding the monoclonal antibody is cDNA. In some instances, the encoding cDNA is integrated into the genome of a host cell. In some instances, the encoding cDNA is episomal. In some embodiments, the nucleic acid molecules encoding the monoclonal antibody is mRNA. In some instances, the uridine residues in the mRNA are substituted with a modified nucleoside, for example, pseudouridine. In some instances, an isolated mRNA is formulated in a lipid nanoparticle. In some embodiments, the nucleic acid sequence encoding the light chain and the heavy chain are contained within a single nucleic acid molecule. In some embodiments, the nucleic acid sequence encoding the light chain and the heavy chain are contained within a separate nucleic acid molecules.

With respect to the above aspects, in some embodiments, the monoclonal antibody that specifically binds aggregated, non-phosphorylated α-synuclein comprises a heavy chain variable domain with HCDR1-HCDR3 having the amino acid sequences of SEQ ID NOs: 7-9, respectively, and a light chain variable domain with LCDR1-LCDR3 having the amino acid sequences of SEQ ID NOS: 13-15, respectively. In some embodiments, the monoclonal antibody that specifically binds aggregated, non-phosphorylated α-synuclein comprises a heavy chain variable domain having the amino acid sequence of SEQ ID NO; 6 and a light chain variable domain having the amino acid sequence of SEQ ID NO: 12. In some embodiments, the monoclonal antibody that specifically binds aggregated, non-phosphorylated α-synuclein comprises a heavy chain having the amino acid sequence of SEQ ID NO; 5 and a light chain having the amino acid sequence of SEQ ID NO: 11. These embodiments constitute means for binding WT-α-syn.

With respect to the above aspects, in some embodiments, an antibody that specifically binds aggregated, non-phosphorylated α-synuclein has a heavy chain and/or a light chain in which one or more of the CDRs have a variant amino acid sequence, wherein the variant CDR sequence(s) are at least 80, 85, 90, or 95% identical to SEQ ID NOs: 7-9 and 13-15, respectively, for HCDR1-2 and LCDR1-3. Amino acid sequence variants of the antibodies are prepared by introducing appropriate nucleotide changes into encoding nucleic acids, or by peptide synthesis. Such variants include, for example, deletions from, and/or insertions into and/or substitutions of, residues within the amino acid sequences of the antibodies of the examples herein. Any combination of deletion, insertion, and substitution is made to arrive at the final construct, provided that the final construct specifically binds aggregated, non-phosphorylated α-synuclein. The amino acid changes also may alter post-translational processes of the variant antibodies, such as changing the number or position of glycosylation sites.

A useful method for identification of certain residues or regions of the antibodies that are preferred locations for mutagenesis is called "alanine scanning mutagenesis". A residue or group of target residues are identified (e.g., charged residues such as Arg, Asp, His, Lys, and Glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecules include the fusion to the N- or C-terminus of the antibody of an enzyme or a polypeptide which increases the serum half-life of the antibody.

Another type of variant is an amino acid substitution variant. These variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Hydrophobic: Norleucine, Met, Ala, Val, Leu, lie;
(2) Neutral hydrophilic: Cys, Ser, Thr;
(3) Acidic: Asp, Glu;
(4) Basic: Asn, Gin, His, Lys, Arg;
(5) Residues that influence chain orientation: Gly, Pro; and
(6) Aromatic: Trp, Tyr, Phe.

Non-conservative substitutions will entail exchanging a member of one of these classes for another class.

Any cysteine residue not involved in maintaining the proper conformation of the antibodies also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identified hypervariable region residues contributing significantly to antigen binding. Alternatively, or in addition, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of an antibody that specifically binds aggregated, non-phosphorylated α-synuclein.

It has been observed that not all CDRs, or the original light chain, are necessarily required to maintain antibody binding specificity. In some embodiments, the antibody that binds aggregated, non-phosphorylated α-synuclein has a heavy chain comprising one or two, but not all three, of SEQ ID NOs: 7-9 and/or a light chain comprising one or two, but not all three, of SEQ ID NOs:13-15. In other embodiments, the antibody that binds aggregated, non-phosphorylated α-synuclein comprises only the heavy chain of the herein disclosed antibodies, or comprises the heavy chain paired with a light chain not previously associated with specificity for aggregated, non-phosphorylated α-synuclein. In some instances, such an alternative light chain is a kappa light chain. In some instances, such an alternative light chain variable region is derived from germline V-gene IGKV1-110*01, IGKV1-110*02, or IGKV1-117*01.

The antibodies disclosed herein may be produced by recombinant means. Thus, disclosed herein are nucleic acids encoding the antibodies, expression vectors containing nucleic acids encoding the antibodies, and cells comprising the nucleic acid encoding the antibodies. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the antibody sequences are inserted into expression vectors by standard methods. Expression is performed in appropriate prokaryotic or eukaryotic host cells like CHO cells, NSO cells, SP2/0 cells, HEK293 cells, COS cells, PER.C6 cells, yeast, or E. coli cells, and the antibody is recovered from the cells (supernatant or cells after lysis). More recently, the use of mRNA to transform cells in vitro and in vivo to produce a protein of interest has become more widespread. Methods of making and using mRNA for such purposes is described, for example, in US20110143397A1, US20090286852A1, and WO2013102203A1, each of which is incorporated by reference for all that they teach in regard to such purposes.

Accordingly, certain embodiments disclosed herein include a method for the preparation of an an antibody that specifically binds aggregated, non-phosphorylated α-synuclein, comprising the steps of a) transforming a host cell with at least one expression vector comprising nucleic acid molecules encoding the antibody; b) culturing the host cell under conditions that allow synthesis of the antibody molecule; and c) recovering said antibody molecule from the culture.

As used herein, the expressions "cell," "cell line," and "cell culture" are used interchangeably and all such designations include progeny. Thus, the words "transformants" and "transformed cells" include the primary subject cell and cultures derived therefrom without regard for the number of passages. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection can be carried out e.g. by the calcium phosphate precipitation method. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The term "host cell" as used herein denotes any kind of cellular system which can be engineered to generate the antibodies disclosed herein. In one embodiment HEK293 cells and CHO cells are used as host cells.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Similarly, in some instances an intron may be present between nucleic acid sequences that are operably linked. Linking is accomplished by ligation at convenient restriction sites. If such sites do not exist, then synthetic oligonucleotide adaptors or linkers are used in accordance with conventional practice.

For recombinant production of the antibodies, the nucleic acid encoding it may be isolated and inserted into a replicable vector for further cloning (amplification of the DNA) or for expression. In some embodiments, the antibody may be produced by homologous recombination, e.g. as described in U.S. Pat. No. 5,204,244, specifically incorporated herein by reference for all it discloses regarding antibody production. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615, specifically incorporated herein by reference for all it discloses regarding protein expression.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *S. typhimurium*, *Serratia*, e.g., *S. marcescans*, and *Shigella*, as well as Bacilli such as *B. subtilis* and *B. licheniformis*, *Pseudomonas* such as *P. aeruginosa*, and *Streptomyces*. One exemplary *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), K. *bulgaricus* (ATCC 16,045), K. wickeramii (ATCC 24,178), *K. waltii* (ATCC 56,500), K. *drosophilarum* (ATCC 36,906), *K. thermotolerans*, and *K. marxianus*; *Yarrowia* (EP 402,226); *Pichia pastoris* (EP 183,070); *Candida*; *Trichoderma* reesia (EP 244,234); *Neurospora crassa*; *Schwanniomyces* such as *S. occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies are derived from multicellular organisms, including invertebrate cells such as plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *B. mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transformed with the above-described expression vectors for antibody production and cultured in conventional nutrient media modified as appropriate for inducing promoters, selecting transformants, or amplifying the genes encoding the desired sequences.

The host cells used to produce the antibodies may be cultured in a variety of media. Commercially available media such as Ham's F10, Minimal Essential Medium (MEM), RPMI-1640, and Dulbecco's Modified Eagle's Medium (DMEM) are suitable for culturing the host cells. In addition, U.S. Pat. Nos. 4,767,704; 4,657,866; 4,927,762; 4,560,655; or U.S. Pat. No. 5,122,469; WO 90/03430; WO 87/00195; or US Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody composition prepared from the cells can be purified using, for example, hydroxyapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains. Protein G is recommended for all mouse isotypes and for human γ3. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

Various aspects are a hybridoma that produces an antibody that specifically binds aggregated, non-phosphorylated α-synuclein. In some embodiments, the hybridoma is 4B1, ATCC Patent Deposit Number PTA-127017. One aspect is a hybridoma generated by a method comprising immunizing a mouse with a peptide comprising or consisting of amino acid residues 125-133 of α-synuclein (SEQ ID NO: 1), namely YEMPSEEGY (SEQ ID NO: 2), for example, the peptide CYEMPSEEGY (SEQ ID NO: 3). One aspect is a hybridoma that produces an antibody that binds aggregated, non-phosphorylated α-synuclein comprising immunizing a mouse with a peptide comprising or consisting of amino acid residues 125-133 of α-synuclein, namely YEMPSEEGY (SEQ ID NO: 2), for example, the peptide CYEMPSEEGY (SEQ ID NO: 3).

One aspect is an immunoassay utilizing an anti-WT-α-syn antibody to detect or quantitate WT-α-syn. An exemplary, non-limiting immunoassay is an enzyme-linked immunosorbent assay (ELISA). In other embodiments, the immunoassay is an immunohistochemical assay. Immunoassays measure substances, such as analytes, proteins, etc., using the specificity of an antibody to the substance. In some embodiments, the anti-WT-α-syn antibody is the antibody produced by the hybridoma is 4B1, ATCC Patent Deposit Number PTA-127017. In some embodiments, the immunoassay may further utilize an antibody specific for pS129-α-syn.

One aspect is a sandwich ELISA. In such an assay, a capture antibody specific for the substance is associated with a solid support, such as a microtiter plate. A liquid containing the substance (or suspected of containing the substance, or a sample in need of determining not to include the substance) is allowed to bind to the capture antibody. Then a detection antibody, also specific for the substance, is added to allow detection of substance bound to the capture antibody. In some embodiments, the anti-WT-α-syn antibody is coated on the surface of a microtiter well or bead and used as the capture reagent and a pan-α-syn antibody is used as the detection reagent. In other embodiments, a pan-α-syn antibody is used as the capture reagent and the anti-WT-α-syn antibody is used as the detection reagent. In some embodiments, the pan-α-syn antibody is 11D12 (Majbour et al., Mol Neurodegener. 11, 7, 2016)

Another aspect is an immunohistochemical assay. Immunohistochemistry involves the process of selectively imaging antigens (proteins) in a tissue section by exploiting the principle of antibodies binding specifically to antigens in biological tissues. Visualizing an antibody-antigen interaction can be accomplished in a number of ways. In the most common instance, a detection antibody is used which allows the detection of the anti-α-synuclein antibody and thus the substance to which the antibody is bound.

In some embodiments, the detection antibody is a labeled antibody. In other embodiments, the anti-α-synuclein antibody is labeled. The label can include a radioactive label, an enzyme label, a colorimetric label, a fluorescent label, a chemiluminescent label, or other labels known to persons of skill in the art. In some such embodiments, the detection antibody is biotinylated so that it can bind an enzyme-linked avidin molecule, such as streptavidin conjugated with horseradish peroxidase or alkaline phosphatase. In alternative embodiments, avidin molecule is conjugated with another detectable label, for example, a fluorescent dye or quantum dot. In some embodiments, the detection antibody is directly labeled. Still further alternatives are familiar to one of skill in the art.

In further embodiments in which the anti-α-synuclein antibody is labeled, the anti-α-synuclein antibody is used for in vivo imaging by administering the labeled anti-α-synuclein antibody to a subject and detecting the label.

In some embodiments, the label is an enzymatic label such as a peroxidase (e.g., horseradish peroxidase), a galactosidase (e.g., β-D-galactosidase), or a phosphatase (e.g., alkaline phosphatase). For enzymatic labels, a substrate is needed which is cleaved by the enzyme to produce a color, fluorescence, or luminescence, which is measured spectrophotometrically. Exemplary colorimetric substrates for peroxidase include, but are not limited to, 3,3',5,5'-tetramethylbenzidine (TMB), 3,3',4,4' diaminobenzidine (DAB), 4-chloro-1-naphthol (4CN), 2,2'-azino-di [3-ethylbenzthiazoline]sulfonate (ABTS), and o-phenylenediamine (OPD). In some embodiments, when the assay is an ELISA, the substrate is TMB which produces a blue color which is measured at a wavelength of 650 nm. The reaction can be halted by addition of acid or another stop reagent. Using a sulfuric acid stop solution turns TMB yellow and the color can then be read at 450 nm. Exemplary colorimetric substrates for phosphatase include, but are not limited to, 5-bromo-4-chloro-3-indolyl-phosphate/nitroblue tetrazolium (BCIP/NBT) and p-nitrophenylphosphate (p-NPP). Exemplary colorimetric substrates for galactosidase include, but are not limited to, 5-dodecanoylaminofluorescein di-3-D-galactopyranoside (C12FDG), 9H-(1,3-dichloro-9,9-dimethylacridin-2-one-7-yl), and β-D-galactopyranoside (DDAO galactoside). Exemplary fluorescent substrates include, but are not limited to, 4-methylumbelliferyl phosphate (4-MUP; for phosphatase), and 4-methylumbelliferyl galactoside (MUG; for galactosidase), fluorescein di-β-D-galactopyranoside (FDG; for galactosidase), hydroxyphenylacetic acid (HPA; for peroxidase), and 3-p-hydroxyphenylproprionic acid (HPPA; for peroxidase). Exemplary luminescent substrates include, but are not limited to, luminol, polyphenols (e.g., pyrogallol, pupurogallin, gallic acid, and umbelliferone) and acridine esters, and luciferin for peroxidase; 3-(2'-spiroadamantane)-4-methyl-4-(3'-phosphoryloxyphenyl-1, 2-dioxetane, disodium salt) (AMPPD) for phosphatase; and (3-(2'-spiroadamantane)-4-methoxy-4-(3'-β-D-galactopyranosyloxyphenyl-1,2-dioxetane (AMPGD) for galactosidase.

In some embodiments, the label is horseradish peroxidase and the substrate is TMB.

In some embodiments, the label is a colorimetric label, a fluorescent label, or a luminescent label. An exemplary colorimetric label includes, but is not limited to, nanoparticulate gold. Exemplary fluorescent labels include, but are not limited to, ethidium bromide, fluorescein and its derivatives, rhodamine and its derivatives, green fluorescent protein, Texas Red, Cascade Blue, Oregon Green, Marina Blue, an atto label, a CF™ dye, an Alexa Fluor, and a cyanine dye. Exemplary luminescent labels include, but are not limited to, luciferin and firefly luciferase.

With respect to the assay aspects, some embodiments the assay is used as a diagnostic assay to determine whether or not an individual has a neurodegenerative disease associated with α-synuclein, for example, Parkinson's disease, dementia with Lewy bodies, Alzheimer's disease, or multiple system atrophy. In some embodiments, the diagnostic assay comprises adding the antibody to a biological sample from a subject, and detecting the presence or absence of a complex formed between α-synuclein aggregates and the antibody or fragment.

In some embodiments, the method of diagnosing a neurodegenerative disease associated with α-synuclein comprises administering an antibody that specifically binds aggregated, non-phosphorylated α-synuclein to an individual and detecting the presence or absence of α-synuclein aggregates. In alternative embodiments, the method of diagnosing a neurodegenerative disease associated with α-synuclein comprises mixing the antibody with a sample from the patient (for example, biopsied tissue or cerebrospinal fluid (CSF). The presence of α-synuclein aggregates indicates that the individual has a neurodegenerative disease and the absence of α-synuclein aggregates indicates that the subject does not have the neurodegenerative disease.

In one embodiment the method of diagnosing a neurodegenerative disease associated with α-synuclein comprises: adding an antibody that specifically binds aggregated, non-phosphorylated α-synuclein to a sample from an individual; detecting the presence of a complex formed between the α-synuclein aggregates and the antibody; and determining whether or not the individual has a neurodegenerative disease associated with α-synuclein.

Determining whether or not the individual has a neurodegenerative disease can comprise comparing the levels of the antibody-α-synuclein complex formed in a sample with a reference level and determining whether the levels of complexes formed in the sample is greater than a reference level associated with the non-diseased state or less than a reference level associated with a diseased state.

In some embodiments, the antibody that specifically binds aggregated, non-phosphorylated α-synuclein is used to diagnose whether an individual has Parkinson's disease. A CSF sample is taken from the patient, antibody is contacted with the sample in conditions effective to allow complexes to form between the antibodies and aggregated α-synuclein present in the sample, and the presence of the antibody-α-synuclein complexes are then detected. The amount of complexes formed can be measured and compared to a reference level.

A correlation has been shown to exist between CSF α-synuclein oligomers levels and disease severity. Detecting the presence and/or amount of the oligomers or fibrils in the sample can be used to follow the progression and or severity of a neurodegenerative disease, in particular for using the antibodies as a biomarker in Parkinson diseases and other diseases associated with α-synuclein pathologies.

Further embodiments comprise monitoring the progress of a neurodegenerative disease associated with α-synuclein by: adding an antibody that specifically binds aggregated, non-phosphorylated α-synuclein to a sample from an individual and detecting the presence of a complex formed between the α-synuclein aggregates and the antibody The progression or improvement of disease over time can be assessed by determining if levels of the antibody-α-synuclein complexes are increasing or decreasing in comparison to one or more earlier patient samples or to a reference level.

As formation of aggregates of unphosphorylated α-synuclein appear to precede the inclusion of phosphorylated α-synuclein in the aggregates, use of an antibody with specificity for the unphosphorylated form can allow earlier detection of aggregates and earlier diagnosis.

In some embodiments, the antibody that specifically binds aggregated, non-phosphorylated α-synuclein can be used in an ELISA to measure aggregated α-synuclein in CFS. The antibody can be used to measure aggregated α-synuclein in a sample with high sensitivity and specificity compared to ELISA using other antibodies. In particular, an ELISA using the antibody that specifically binds aggregated, non-phosphorylated α-synuclein has a higher sensitivity and specificity to detect unphosphorylated α-synuclein oligomers and protofibrils in CSF as compared to an ELISA using monoclonal antibodies without this specificity as a capture antibody and/or detection antibody.

The methods can be used to monitor the effectiveness of a therapeutic agent, by using the results of the analysis undertaken. An effective therapeutic agent can be determined as one that causes a decrease in the amount of α-synuclein aggregates present in a sample taken from the patient, as compared to a reference value. The reference value may reflect the amount of α-synuclein in the patient before treatment, or may represent a typical amount of α-synuclein to be found in untreated patients.

With respect to the assay aspects, some embodiments comprise a test kit comprising an anti-α-synuclein antibody and other reagents or equipment needed to carry out the assay.

EXAMPLES

The following non-limiting examples are provided for illustrative purposes only in order to facilitate a more complete understanding of representative embodiments now contemplated. These examples should not be construed to limit any of the embodiments described in the present specification, Example 1

Generation of Monoclonal Antibody Recognizing Non-Phosphorylated S129-α-Synuclein (WT-α-Syn) Aggregates A short synthetic peptide, CYEMPSEEGY (SEQ ID NO:3), designed over the region of interest (amino acids 125-133 of α-syn; YEMPSEEGY (SEQ ID NO:2)), was used as the immunogen. This peptide was solubilized in phosphate-buffered saline (PBS) and conjugated to keyhole limpet hemocyanin (KLH) as carrier protein. Experimental procedures using mice were carried out in accordance with Laboratory Animal Research Center (LARC), Qatar University (QU), Qatar, according to the QU institutional ethical rules and regulations and approved by QU—IACUC & IBC. Specifically, female BALB/c mice (6-8 weeks old) were injected subcutaneously with the immunogen conjugate. Ten days post booster immunization, blood was collected from the tail vain and titer response was evaluated using indirect ELISA. Mice exhibiting a strong immune response were subjected to a final immunization before euthanization. Following hybridoma generation, monoclonal antibodies specific for WT-α-syn were obtained. Culture supernatants were tested for secreted anti-α-syn antibodies using indirect ELISA.

For the indirect ELISA, a 96-well clear plate was coated with recombinant WT-α-syn and incubated overnight at 4° C. The following day, the plate was blocked with blocking buffer (PBST containing 2.25% gelatin) for 1 hour at RT. The plate was then washed three times with PBST, and antisera from the mice, or culture supernatants, were added in serial dilutions. Next, the plate was washed and goat anti-mouse IgG-HRP (1:20 K, Jackson ImmunoResearch) was added. The plate was washed again and detected with TMB substrate (Abcam). Following color development, the reaction was stopped by addition of 0.6 N $H_2SO_4$ and the absorbance was measured at 450 nm.

To generate hybridoma, splenocytes were fused with mouse myeloma cells (Sp2O—Ag14; American Type Culture Collection) at a ratio of 5:1 and fusion was induced using 50% polyethylene glycol. Fused cells were seeded in 96-well plate in IMDM media (Gibco) containing HAT (Sigma). Positive clones were transferred to 24-well plates and screened multiple times to ensure stability.

For isotyping, culture supernatant was screened against anti-mouse heavy chain antibodies (Isotyping Kit, Sigma-Aldrich) in ELISA and only IgG-positive clones were selected. Those were subjected to single-cell cloning. Wells with single clones were grown to confluency and screened at least three times for further selection of stable clones. Selected clones were grown in CDM4mAb media (Hyclone) to confluency. Culture supernatant was then collected and purified using protein-G agarose affinity chromatography (Sigma-Aldrich). Several monoclonal antibodies were produced, purified and thoroughly characterized. An IgG1 monoclonal antibody designated 4E1 was selected for further characterization.

Figure 12A:
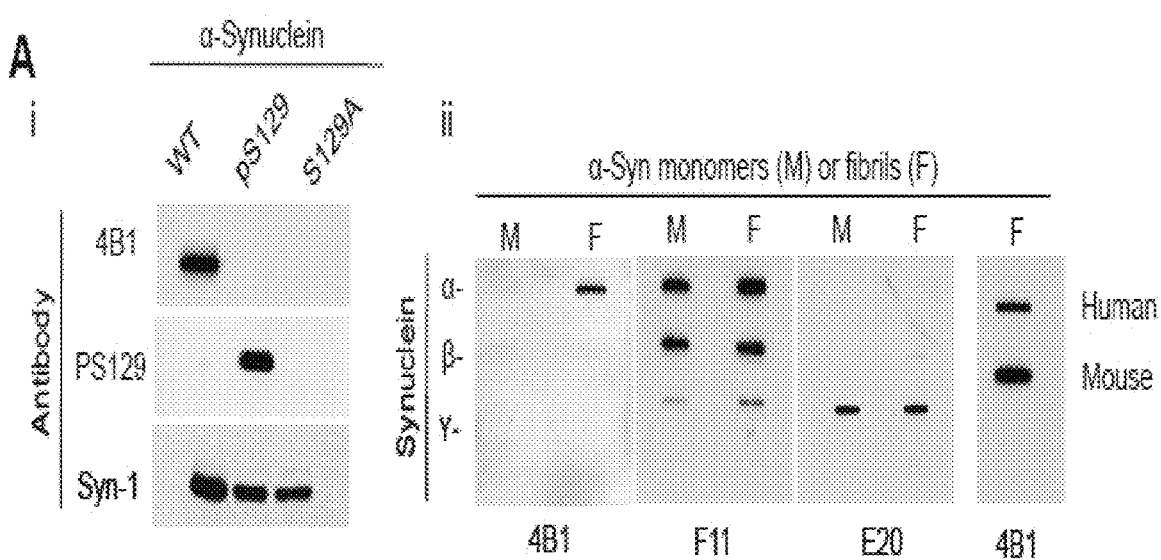

The purity of 4E1 antibody was assessed using SDS-PAGE under reducing conditions. The specificity of 4E1 for recombinant WT-, pS129-, or mutated S129A-α-syn (with a substitution of serine 129 to alanine) proteins was assessed by western blot. The data showed that 4E1 is specific for WT-α-syn and did not recognize pS129-α-syn (FIG. 12A panel i). Furthermore, there was no evident band when serine was replaced with alanine (S129A-α-syn) indicating that S129 is an integral residue of 4E1's epitope (FIG. 12A, panel i). Syn-1 (mouse anti-α-syn, BD Bioscience) and PS129 (in-house mouse anti pS129-α-syn antibody (Majbour et al., *Mol Neurodegener.* 11(7), 2016), antibodies were included as controls (FIG. 12A, panel i). Filter retardation assay analysis showed that 4E1 specially recognized α-syn sparing β- and γ-syn (FIG. 12A, panel ii). F11 (mouse monoclonal anti-α/β/γ synuclein antibody, Santa Cruz Biotechnology), E-20 (mouse monoclonal anti-γ-syn antibody, Santa Cruz Biotechnology) were included as control antibodies. 4B1 recognized both human and mouse α-syn to equal extent (FIG. 12A, panel ii). Additionally, 4B1 reacted equally to WT-α-syn from human or mouse species.

Hybridoma 4B1 was deposited with the American Type Culture Collection, 10801 University Boulevard, Manassas VA, 20110-2209 on Jun. 24, 2021 and given the Patent Deposit Number (accession number) PTA-127017.

Example 2

Specificity of 4B1 Towards WT-α-Syn Aggregates

Using filter retardation assay, an assay that preserves the protein conformation, surprisingly we found that 4B1 only recognized WT-α-syn aggregates, and did not recognize the monomeric form of α-syn protein (FIG. 12Bi). Syn-02 (a mouse monoclonal antibody against α-syn aggregates (Vaikath et al., *Neurobiol Dis.* 79:81-99, 2015)), and Syn-1 were used as control antibodies (FIG. 12B, panel i).

Given that α-syn undergoes different conformational changes forming oligomers and amyloid fibrils, we further assessed the specificity of 4B1 antibody against different conformations of the protein. α-Syn oligomers were prepared in vitro either through spontaneous formation during α-syn fibrillization, or in the presence of a cross-linking reagent such as the lipid peroxidation products 4-oxo-2- nonenal (ONE) or 4-hydroxy-2-nonenal(HNE). Both oligomers hold distinct compositions and conformations (Uversky, Cell Mol Life Sci. 60(9):1852-1871, 2003; Pieri et al., Sci Rep. 6(24526), 2016). 4B1 showed higher affinity towards beta-sheet rich aggregates (fibrils, ONE-, or HNE-oligomers) (FIG. 12B, panel i). To further evaluate the selectivity and affinity of 4B1 antibody towards α-syn aggregates we performed an inhibition ELISA. Our data showed that 4B1 antibody selectively recognized oligomers compared to monomers (FIG. 12Bii). 4B1 was also tested against serial dilutions of α-syn monomers, ONE- and HNE-oligomers, and pS129-α-syn aggregates using sandwich-based ELISA assay. Affirming previous observations, 4B1 specifically recognized α-syn oligomers sparing both the monomeric and phosphorylated forms (FIG. 12B, panel iii). Altogether, the data strongly suggests that 4B1 is specific for beta-sheet rich aggregates of WT-α-syn.

Example 3

PS129 α-Syn Inhibits α-Syn Aggregation

Knowing that under physiological conditions only 4% of α-syn is phosphorylated at S129, we investigated the effect of pS129-α-syn on α-syn aggregation. Pure monomeric α-syn was mixed with different concentrations of pS129-α-syn (0-100%). Samples were incubated up to 20 days, and Th—S binding assay showed the aggregation at various time points. As expected, the non-phosphorylated monomeric α-syn aggregated gradually reaching approximately 35,000 Th—S counts after 20 days of incubation (FIG. 1A). The sample containing 5% pS129-α-syn exhibited a similar aggregation trend to the non-phosphorylated sample (FIG. 1A). Surprisingly, the sample with 20% of pS129-α-syn showed a significant decrease in aggregation, given that the reduction in Th—S fluorescence readings was more than 50%. Moreover, the fibril formation in the samples containing 50% and 100% of pS129-α-syn was almost depleted, with Th—S fluorescence readings reaching approximately 2,000 counts after 20 days of incubation. The results indicate that phosphorylation at S129 exerts an inhibitory effect on α-syn aggregation.

Example 4

PS129 α-Syn has Reduced Ability to Seed the Aggregation of α-Syn

Figure 8A:
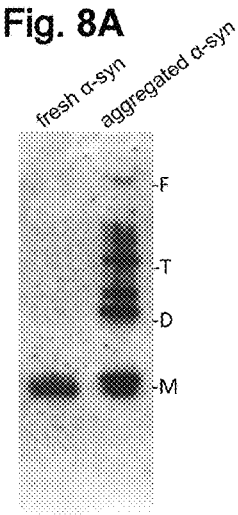
FIGS. 8A-E depict characterization of in vitro prepared pS129-α-syn.
Figure 8B:
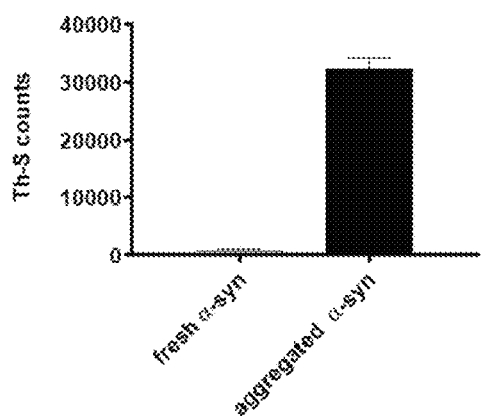
Figure 8C:
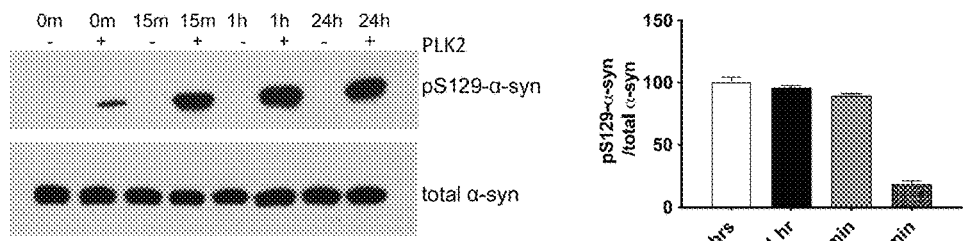
Figure 8D:
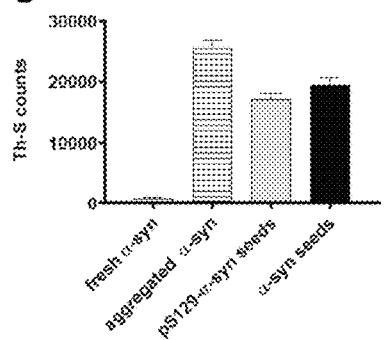
Figure 8E:
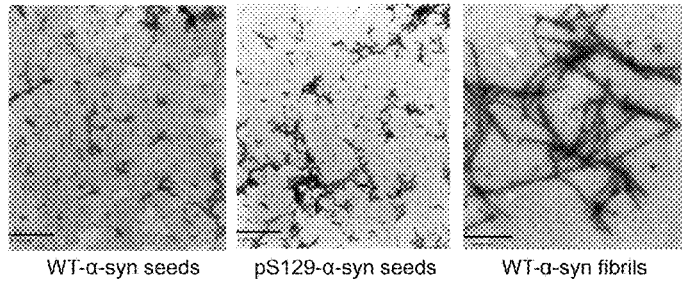

We further assessed whether pS129-α-syn had an effect on seeding α-syn aggregation. For this purpose, in vitro phosphorylated monomeric and aggregated recombinant α-syn (characterized by immunoblotting and Th—S binding (FIG. 8A, 8B) were utilized. The phosphorylation of α-syn was confirmed by immunoblotting with a pS129-α-syn specific antibody (FIG. 8C). WT and pS129-α-syn pure seeds were characterized by Th—S fluorescence and EM (FIG. 8D, 8E). Upon addition of WT-α-syn seeds (2 μM), monomeric α-syn aggregation was dramatically accelerated as shown by increasing Th—S fluorescence readings throughout the incubation period compared to monomeric α-syn alone (FIG. 1B). It is worth noting that WT-α-syn seeds (2 μM) had a greater impact on the aggregation of monomeric α-syn compared to pS129-α-syn seeds (FIG. 1B). However, upon addition of seeds at lower concentration (0.1 μM), pS129-α-syn seeds completely failed to aggregate WT-α-syn monomers, whereas, WT-α-syn seeds at the same concentration significantly accelerated the monomeric α-syn aggregation (FIG. 1C). Moreover, we studied the seeding effect of pS129-α-syn monomers. The data illustrated that pS129-α-syn monomers failed to aggregate even after 48 hours of incubation after adding either WT-α-syn seeds or pS129-α-syn seeds, indicating that phosphorylation at S129 had an inhibitory effect on α-syn aggregation (FIG. 1D, E).

Example 5

Inhibitory Seeding Effect of PS129-α-Syn on RT-QuIC Assay

Next, we evaluated the impact of phosphorylation at S129 on the seeded nucleation-dependent polymerization assay (RT-QuIC) for α-syn (Fairfoul et al., Ann Clin Trans/Neurol. 3(10):812-818, 2016). This assay was carried out in the temporal and frontal cortex samples extracted from four PD and four DLB cases. We performed the assay using WT- and pS129-α-syn monomers. Interestingly, as shown in FIG. 2, monomeric WT-α-syn showed higher seeding propensity compared to pS129-α-syn that remained negative with the unseeded reaction (FIG. 2A-H). This data confirmed the inhibitory effect of pS129 modification on α-syn aggregation. α-Syn seeding activity was detected in all the cases where WT-α-syn was used as substrate (FIG. 2A-H). To better characterize the RT-QuIC efficiency and simplify the results for comparison, we assessed the RT-QuIC kinetic parameters of the reactions seeded with brain homogenates. When compared to pS129-α-syn, WT-α-syn showed the shortest lag-times (FIG. 2F, Table 1), the highest amyloid formation rates (FIG. 2G) and the highest FMAX (FIG. 2H).

TABLE 1

RT-QuIC kinetic parameters of the relative seeding activity for monomeric α-syn/pS129-α-syn in frontal and temporal regions extracted from PD and DLB cases.

| Seed | Substrate | lag-phase ± stdev | Amyloid formation rate ± st dev (1/hours) | $F_{MAX}$ (RFU × 10$^3$) ± stdev |
|---|---|---|---|---|
| PD Frontal | α-syn | 26 ± 3.4 | 0.04 ± 0.005 | 180 ± 57 |
| | pS129-α-syn | 94 ± 45 | 0.013 ± 0.008 | 69.8 ± 58.7 |
| PD Temporal | α-syn | 19.8 ± 2.5 | 0.05 ± 0.006 | 199 ± 34.8 |
| | pS129-α-syn | 104 ± 34 | 0.01 ± 0.003 | 32.2 ± 5 |
| DLB Frontal | α-syn | 37.8 ± 6 | 0.027 ± 0.005 | 131 ± 93 |
| | pS129-α-syn | 132 ± 31 | 0.007 ± 0.0019 | 27.7 ± 4 |
| DLB Temporal | α-syn | 22.5 ± 4 | 0.045 ± 0.008 | 259 ± 0.571 |
| | pS129-α-syn | 88 ± 45 | 0.013 ± 0.006 | 118 ± 99 |

Example 6

Figure 3A:
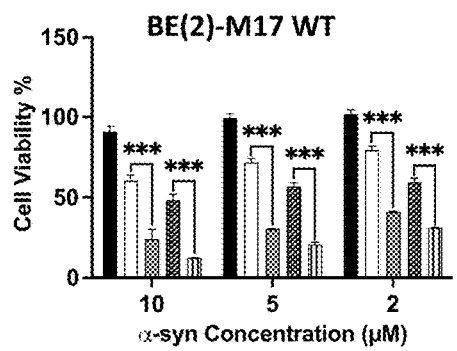
FIGS. 3A-D depict the effect of WT- and pS129-α-syn seeding on the viability of neuroblastoma cells. The effect of WT and pS129-α-syn seeding on the viability of BE(2)-M17-WT (FIGS. 3A, 3C) and SH-SY5Y human neuroblastoma WT (FIGS. 3B, 3D) cells was estimated by the MTT assay. BE(2)-M17 (FIGS. 3A, 3C) and SH-SY5Y (FIGS. 3B, 3D) cells were treated with different concentrations of α-syn pure fibrils or pure seeds and one hour after treatment, monomeric WT or pS129-α-syn was added to a final concentration of 10 µM for 48 hours (average of 3 wells±standard deviation). The results are expressed as the percentage of the control average (i.e., untreated cells). (*, $p<0.001$; , $p<0.01$, *, $p<0.05$).
Figure 3B:
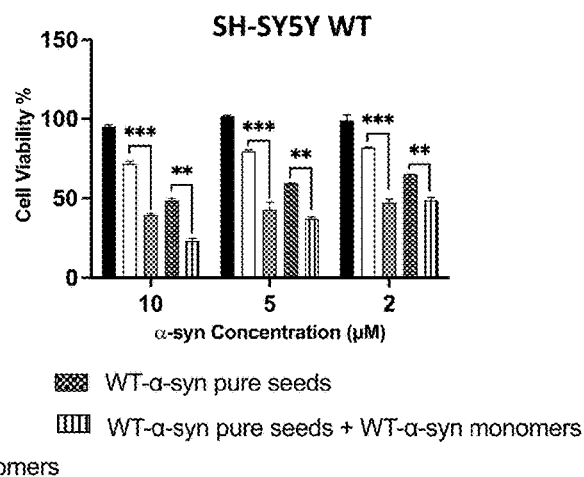
Figure 9A:
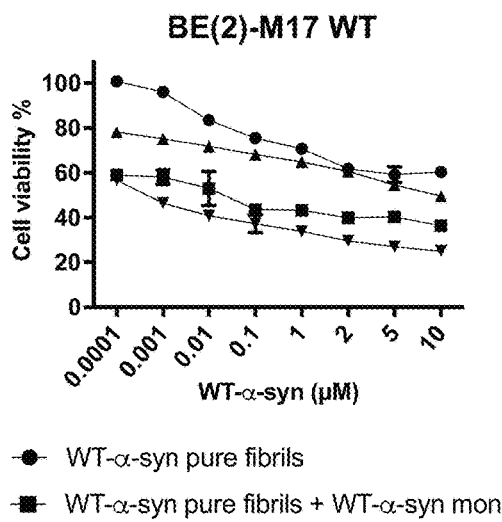
FIGS. 9A-D depict the effect of α-syn seeding on the viability of neuroblastoma cells. The viability of BE(2)-M17 and SHSY-5Y WT human neuroblastoma cells was estimated by the MTT assay. The results are expressed as the percentage of the control average (i.e., untreated cells). BE(2)-M17 (FIG. 9A) and SHSY-5Y WT (FIG. 9B) cells were treated with different concentrations of α-syn pure fibrils or pure seeds (0.0001-10 µM) and one hour after treatment, monomeric α-syn to a final concentration of 10 µM of was added. BE(2)-M17 (FIG. 9C) and SHSY-5Y (FIG. 9D) cells were treated with 2 µM (final concentration) of α-syn pure fibrils or pure seeds and one hour after treatment, monomeric α-syn was added to a final concentration ranging between 1-20 µM. The assay was performed in triplicates and the means±standard deviation are shown.
Figure 9B:
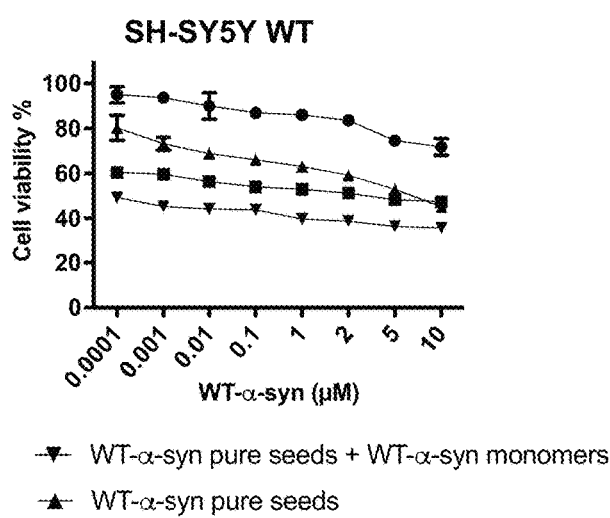
Figure 9C:
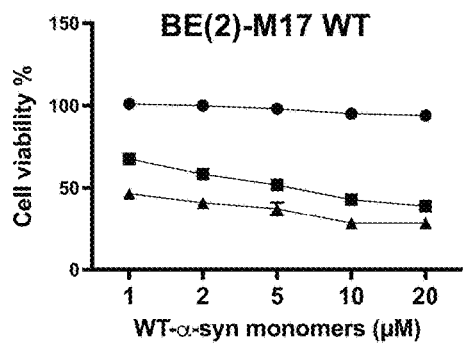
Figure 9D:
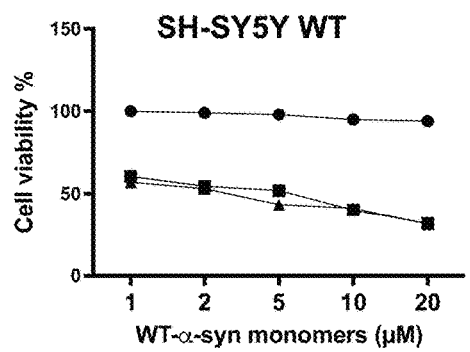

Addition of PS129-α-Syn Monomers to Preformed Aggregates in Cells Did not Promote Seeding-Mediated Toxicity The cytotoxicity effect of pure seeds and fibrils (2, 5 and 10 μM) on BE(2)-M17 and SH-SY5Y WT cells in the presence or absence of WT-α-syn monomers was evaluated. Both α-syn species affected cell viability (both BE(2)-M17 and SH-SY5Y) at all tested concentrations as shown in FIGS. 3A and B. Despite the fact that seeds exhibited more toxicity than fibrils, adding monomeric WT-α-syn significantly exacerbated this effect. Given that the effect was independent of pure seeds/fibrils concentration, cellviability was evaluated upon varying both the concentration of seeds and fibrils (lower concentration scale, of 0.0001-10 µM) in the presence of a constant concentration of α-syn monomers and vice versa (FIG. 9). As shown in FIG. 9A, 9B, pure seeds and fibrils decrease cell viability in a concentration-dependent fashion, with a more pronounced toxic effect in the presence of monomeric α-syn (final concentration of 10 µM), with seeds being more toxic than fibrils. Additionally, different concentrations of monomeric α-syn (1-20 µM) on cell viability were assessed, with cells first treated with a constant concentration (2 µM) of either pure fibrils or seeds. As indicated in FIG. 9C, 9D, the addition of monomers seems necessary for cell toxicity when pre-treated with pure fibrils or seeds since α-syn monomers alone had no effect.

Figure 10A:
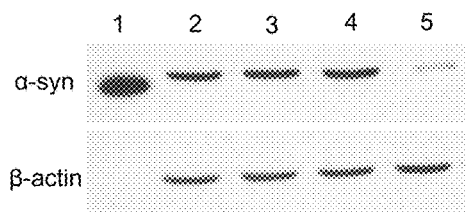
FIGS. 10A-E depict the effect of pure seeds and fibrils on neuroblastoma cells with knocked down endogenous α-syn. The cell viability of BE(2)-M17 cells, whose endogenous α-syn has been knocked down was studied by the MTT assay. Pre-designed siRNA sequence targeting human WT-α-syn was used to silence the expression of α-syn, and non-targeting scrambled siRNA was used as negative control.
Figure 10B:
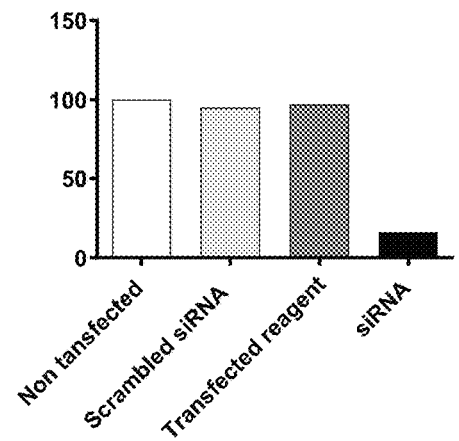
Figure 10C:
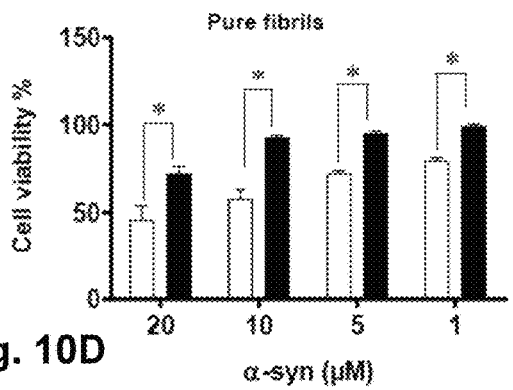
Figure 10D:
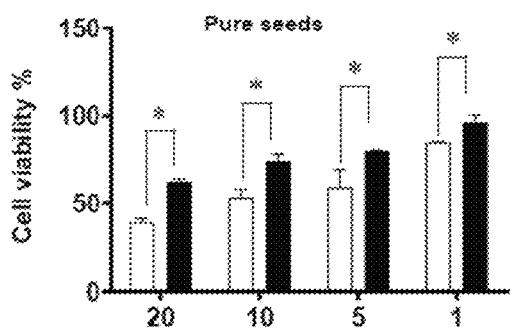
Figure 10E:
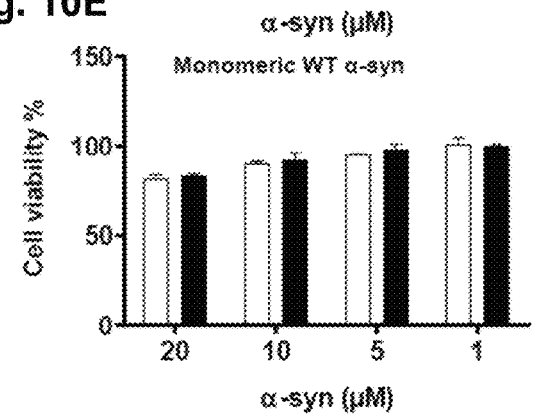

To further emphasize the role of monomeric α-syn in inducing the nucleation polymerization process of α-syn, the effect of pure seeds and fibrils on the viability of BE(2)-M17 WT cells with siRNA silenced endogenous α-syn was also examined. Immunoblotting and its corresponding quantification of α-syn expression are shown in FIG. 10A, 10B. The results demonstrated that the cells whose endogenous α-syn was knocked down were less susceptible to the toxic effects of pure fibrils (FIG. 10C) and seeds (FIG. 10D). However, the treatment of cells with monomeric α-syn at all given concentrations had similar effects in siRNA-transfected and control cells (FIG. 10E). The data confirm the important role of monomeric α-syn in aggregation-induced toxicity.

Figure 3C:
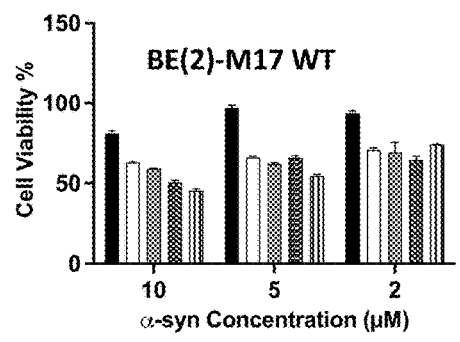
Figure 3D:
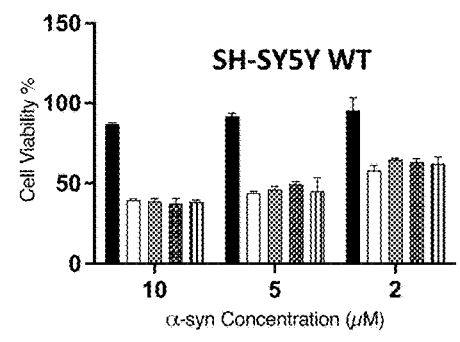
Figure 11A:
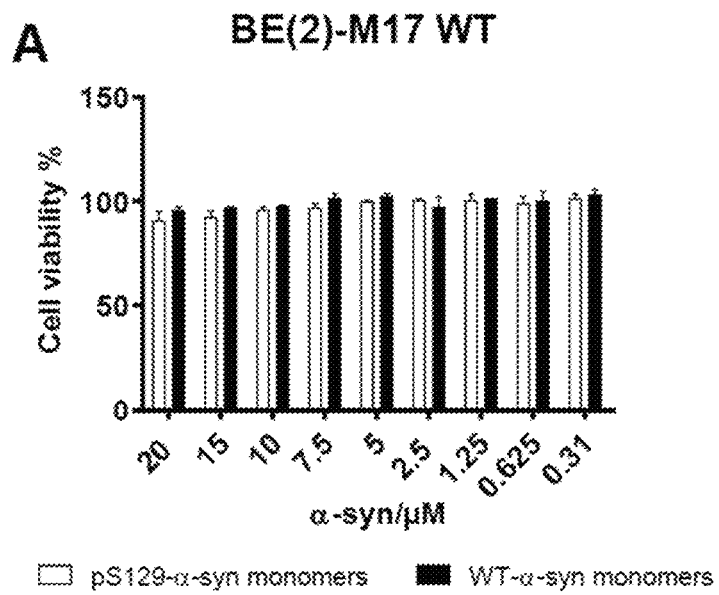
FIGS. 11A-B depict the effect of monomeric pS129-α-syn on the viability of neuroblastoma cells. The effect of monomeric WT- and pS129-α-syn on the viability of BE(2)-M17-WT (FIG. 11A) and SHSY-5Y human neuroblastoma WT (FIG. 11B) cells was estimated by the MTT assay. The results are expressed as the percentage of the control average (i.e., untreated cells). The assay was performed in triplicates and the means±standard deviation are shown.
Figure 11B:
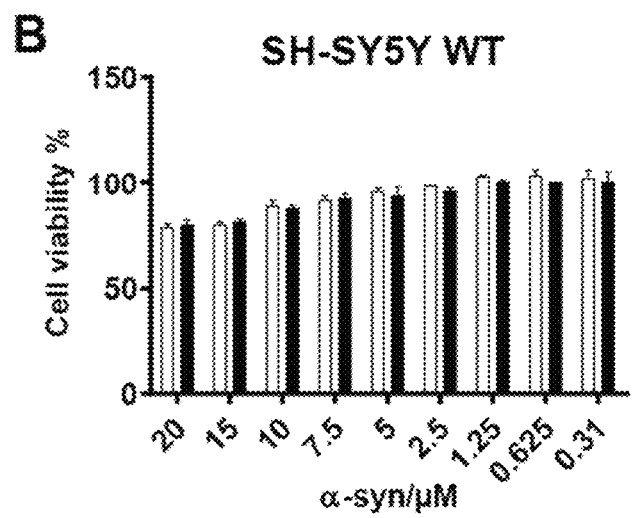

Our findings prompted us to study the effect of monomeric pS129-α-syn alone compared to WT-α-syn on the toxicity of both BE(2)-M17 and SH-SY5Y WT cells. Monomeric pS129-α-syn employed at a range of concentrations (0.31-20 µM) did not show toxicity in BE(2)-M17 cells (FIG. 11A) and SH-SY5Y cells (FIG. 11B). For this purpose, adding monomeric pS129-α-syn to cells pre-treated with either pure fibrils or pure seeds was assessed for toxicity. BE(2)-M17 and SH-SY5Y WT cells were treated with different concentrations of either pure fibrils or pure seeds (10, 5 and 2 µM) and after one hour of incubation, monomeric pS129-α-syn was added to the cells at a final concentration of 10 µM. As shown in FIG. 3C, 3D, pS129 monomers had no effect on viability of the cells pre-treated with various concentrations of pure fibrils or seeds. The toxicity levels observed were comparable and statistically non-significant to the group treated only with pure seeds orfibrils.

Figure 4A:
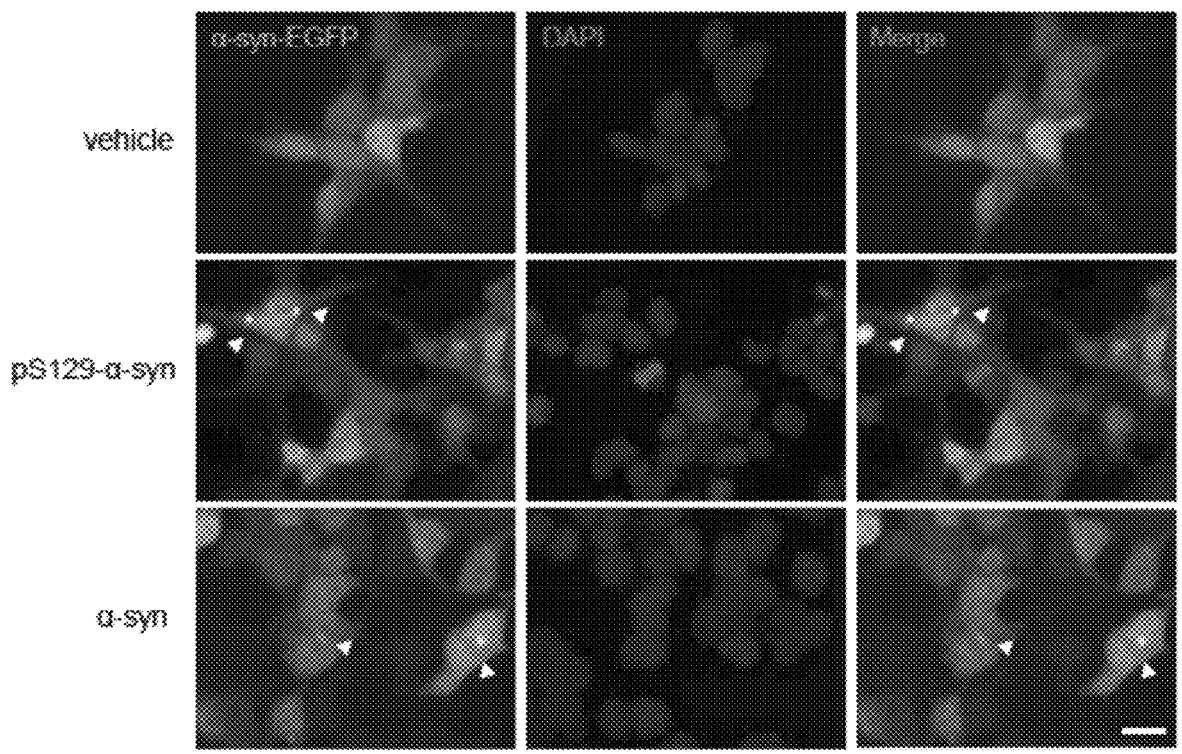
FIGS. 4A-B depict the effect of pS129-α-syn seeds in seeding the aggregation of endogenously expressed α-syn-EGFP.
Figure 4B:
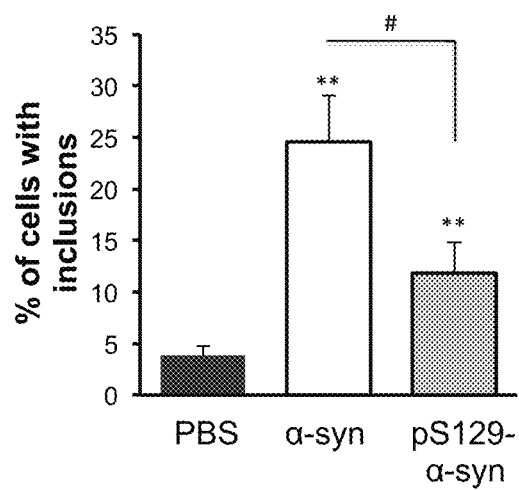

Example 7 pS129-α-syn seeds is less potent in seeding α-syn aqqregation in cells To further investigate the seeding efficiency of α-syn seeds in vitro, we used a stable cell line over-expressing α-syn fused to EGFP (HEK293-aSyn-EGFP) undertheCMV promoter, to examine whether the exogenous addition of the different α-syn seeds affected the seeding of endogenous α-syn. We treated cells with either WT-α-syn seeds or pS129-α-syn seeds at a final concentration of 100 nM and incubated for four days. Control cells were exposed to vehicle only (PBS). Cells were then processed for microscopy and the percentage of cells with intracellular accumulation of α-syn-EGFP was counted. Interestingly, we found that the internalized WT-α-syn seeds resulted in a significant increase of the α-syn-EGFP inclusions, compared to control cells (FIG. 4A). In contrast, exposure of cells to pS129-α-syn seeds caused a significantly lower percentage of cells with α-syn inclusions when compared to the WT-α-syn-treated cells, but yet significantly higher than control cells (FIG. 4B).

Example 8

Figure 13:
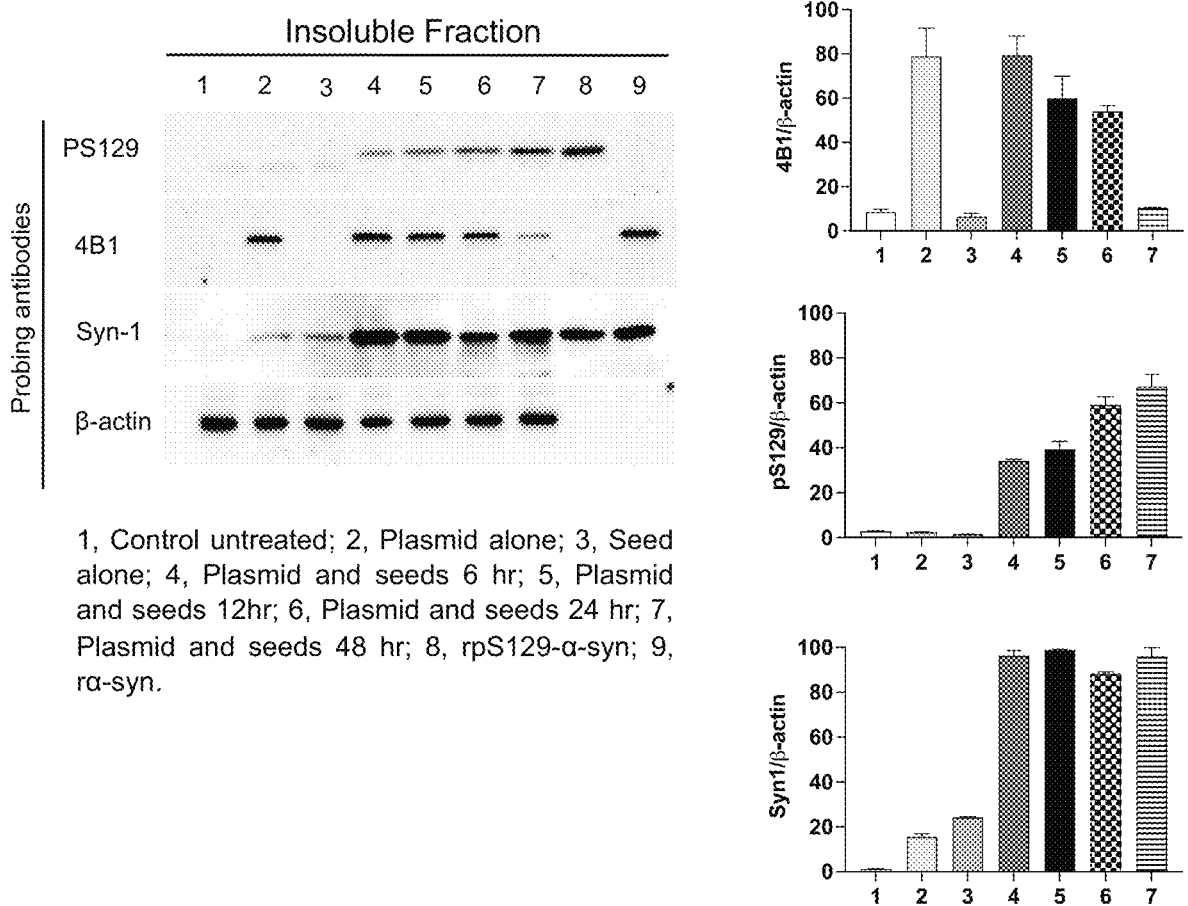
FIG. 13 depicts the effect of S129A-α-syn seeding on aggregation and accumulation of insoluble pS129-α-syn in a HEK cell model. 10 µg of insoluble proteins from cell lysates of untransfected (control) and transfected HEK cells were immunoblotted proteins using antibodies specific to pS129-α-syn and total α-syn (Syn-1) at time points 6, 12, 24, 48 hours post seed transfection. Recombinant pS129-α-syn (rpS129-α-syn) and recombinant α-syn (ra-syn) proteins were loaded (50ng) as positive controls. Re-immunoblotting with β-actin antibody was performed to normalize the amount of loaded proteins.

WT-α-syn is predominant at early stages in a seeding dependent aggregation in vitro model of HEK cells Given the central role of seeding in inducing α-syn fibril formation, seeding-dependent aggregation by mutant S129A-α-syn seeds, and the formation ofinsoluble pS129-α-syn was studied in an in-vitro cell model consisting of α-syn expressing HEK cells. Insoluble pS129-α-syn was induced after a consecutive transfection of WT-α-syn and mutant S129A-α-syn seeds. These results indicate that pS129-α-syn is generated at later stages especially at 24 and 48 hours post seed treatment (FIG. 13). On the contrary, insoluble WT-α-syn detected by 4B1, showed a gradual decrease in its expression with the greatest effect at 48 hours post transfection (FIG. 13). These findings confirm that the levels of the two forms of α-syn protein are inversely related, with insoluble WT-α-syn having its highest formation at early stages and pS129-α-syn appearing at later stages.

Example 9

Figure 5A:
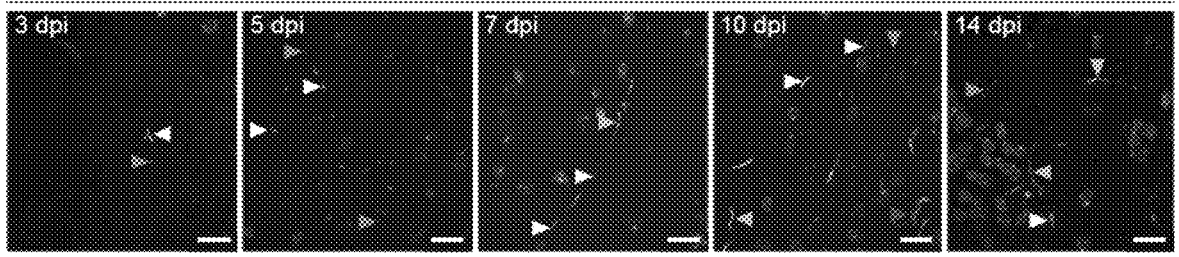
FIGS. 5A-H depict an analysis of α-syn aggregates on organotypic slice culture model after injection of S129A-α-syn PFF.
Figure 5B:
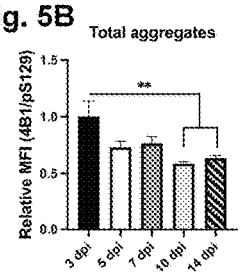
Figure 5C:
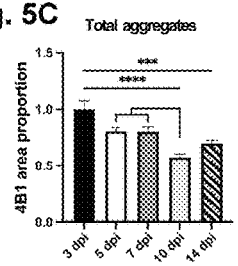
Figure 5D:
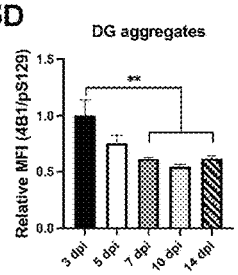
Figure 5E:
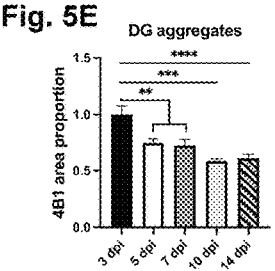

Slice Culture Model Displays a Maturation of Aggregates with Increasing Phosphorylation at S129 Over Time In order to investigate any temporal developments in the structural composition of α-syn aggregates, we employed a recently described organotypic slice culture model where α-syn aggregation is induced by injection of S129A-α-syn PFF (Elfarash et al., *Acta Neuropathol Commun.* 7(213), 2019). Evaluating slices at both early and later time points after induction of aggregation and stained by 4B1 revealed a continuous decrease in both the WT-α-syn—stained proportion of aggregates and in the relative mean fluorescence intensity (MFI) of the WT-α-syn aggregate staining compared with the pS129-α-syn staining (FIG. 5A-C). The same pattern was visible when focusing the analysis on the dentate gyrus (DG), the region in which aggregate formation is induced and is thus by far most abundant (FIG. 5D-E). The decrease in both area proportion and MFI of WT-α-syn (representing the density of staining) effectively highlights an increase in the phosphorylation level of α-syn aggregates overtime, indicating maturation of the aggregates taking place.

Figure 5F:
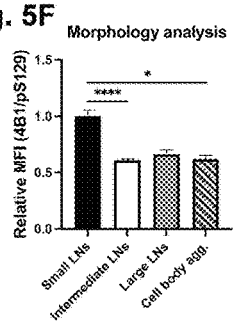
Figure 5G:
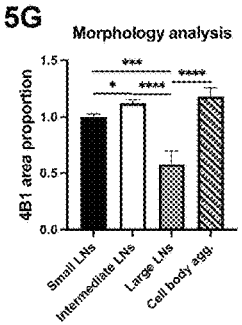
Figure 5H:
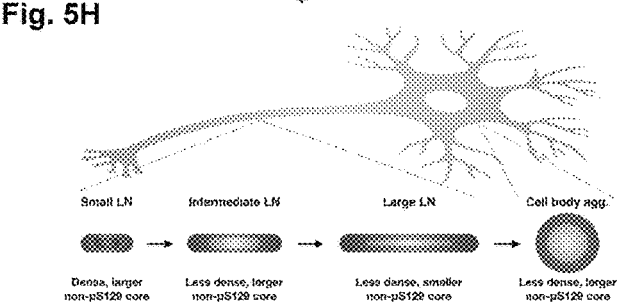
Figure 14:
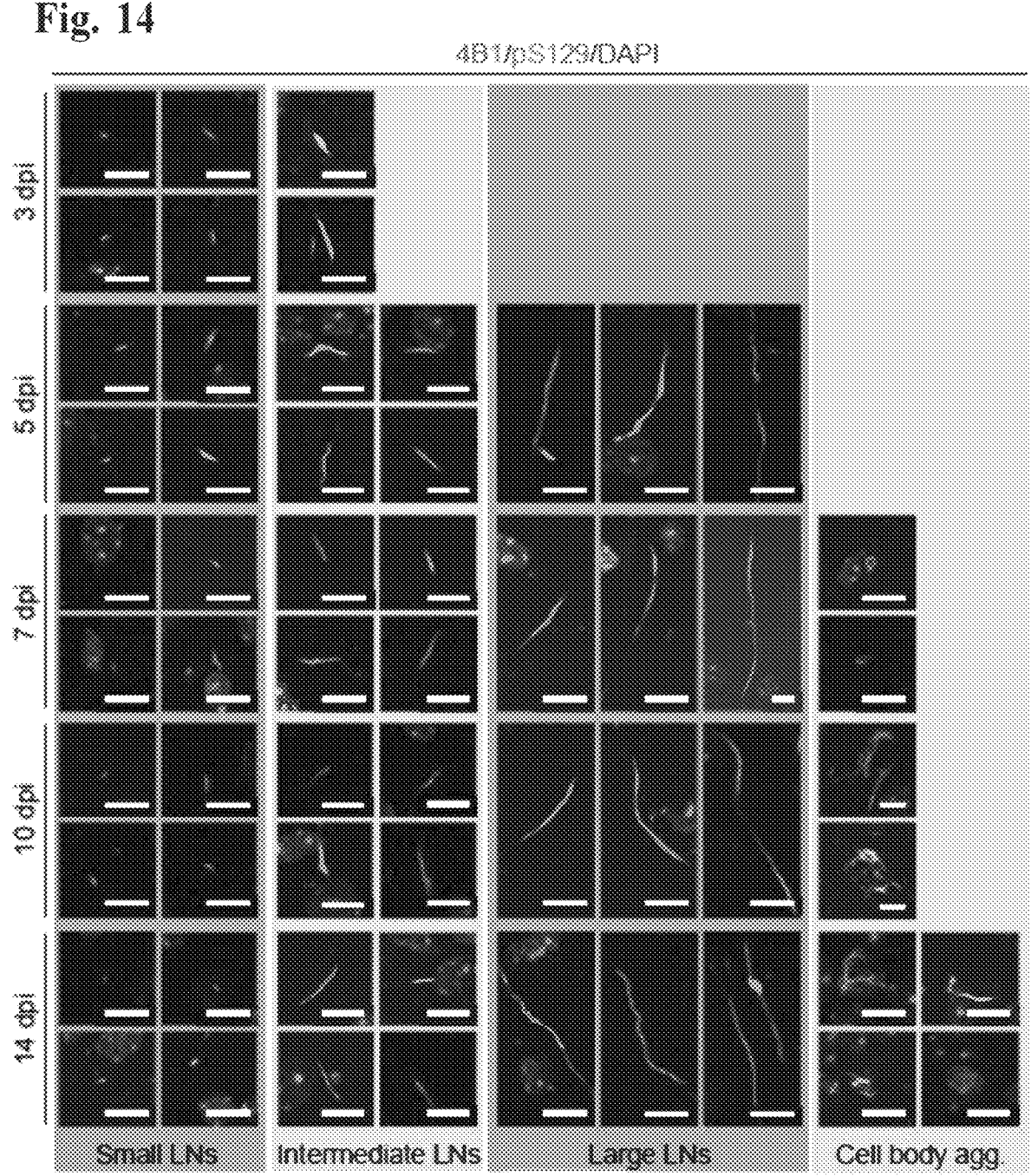
FIG. 14 displays a staining analysis on organotypic slice culture model at early and late time points. Illustrative images of the various types of aggregates (small LNs, intermediate LNs, large LNs and cell body inclusions) at each time point, stained for 4B1 and pS129-α-syn. Scale bars=10 µm. The temporal developments in the structural composition of α-syn aggregates is shown with time advancing from top to bottom, and their morphological development from left to right, progressing though small and intermediate sized Lewy-neurite-like aggregates (LNs), large LNs and cell body inclusions. This figure presents representative images of these four groups of aggregates with respect to different time points, 3, 5, 7, 10, 14 days post injection (dpi) to illustrate the morphological progression. As seen in the images, the predominant form in the early time points (3-5 dpi) are the small and intermediate LNs. On the other hand, at later time points (7-14 dpi), large LNs and cell body inclusions are the prevalent aggregates observed. By checking all existing aggregates, the data shows a common feature which is having a core of WT-α-syn (stained by 4B1 antibody) surrounded by pS129-α-syn (stained by anti-pS129 antibody).

To further investigate this maturation, analysis was stratified against morphology of aggregates, dividing them into four groups. At early time points (3-5 days post injection (dpi)), the predominant aggregate types are small and intermediate sized Lewy-neurite-like aggregates (LNs), while at later time points (7-14 dpi) large LNs and cell body inclusions start appearing. Thus, the changes in WT-α-syn area proportion and relative MFI might reflect differences between the various types of aggregates. Examining the individual aggregate types showed that all aggregate types possessed a core of WT-α-syn, which was surrounded by pS129-α-syn (FIG. 14). Moreover, the relative WT-α-syn MFI of the small LNs was much higher than that of any other type of aggregate (FIG. 5F). Conversely, the area proportion of WT-α-syn in the aggregates was relatively stable between small LNs, intermediate LNs and cell body inclusions, while large LNs displayed a significantly smaller core of WT-α-syn (FIG. 5G). The results thus indicate a maturation process of the aggregates, where small LNs possess a large, dense core of WT-α-syn. In the intermediate LNs, the density of the WT-α-syn core is decreased, but the relative size of the core is unchanged, in contrast with the large LNs, where the core size is decreased while the density of WT-α-syn stays fixed (FIG. 5H). Curiously, cell body inclusions appear to have a larger WT-α-syn core than the large LNs, similar to the intermediate LNs.

Example 10

PS129-α-syn occurs at a late stage in mice injected with α-syn preformed fibrils Immunohistochemical analysis of striatal sections from mice injected with PFFs showed accumulation of WT-α-syn at the early stages, mainly at one and two weeks post injection of PFFs (FIG. 6A). On the contrary, evident formation of pS129-α-syn was not apparent until 4 weeks post injection (FIG. 6A), indicating its occurrence at late phases. For further validation, striatum sections were also subjected to PK treatment. These sections showed that WT-α-syn accumulations were PK resistant as shown at two weeks post injection (FIG. 6B).

Example 11

Figure 7A:
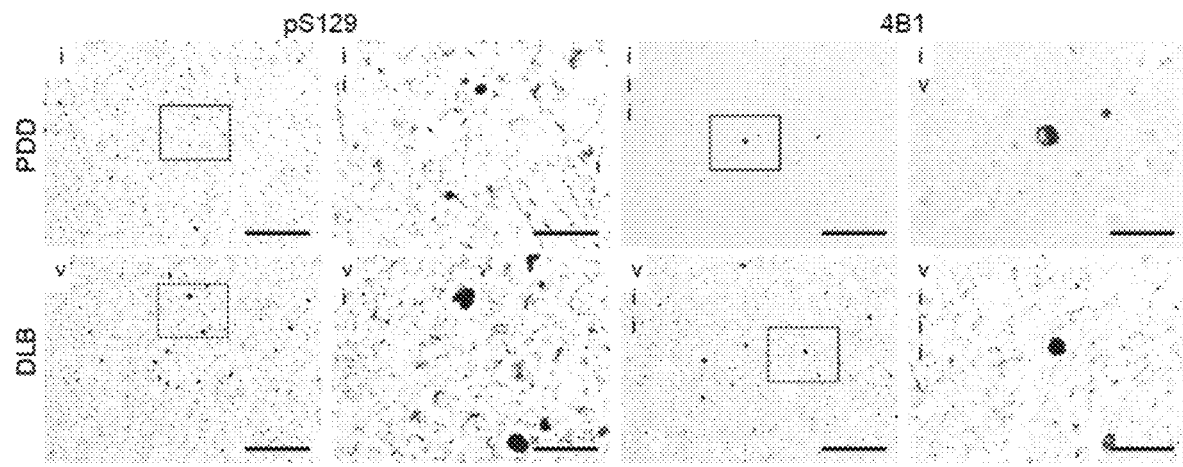
FIGS. 7A-C depicts expression of WT- and pS129-α-syn in post-mortem human brain tissue.
Figure 7B:
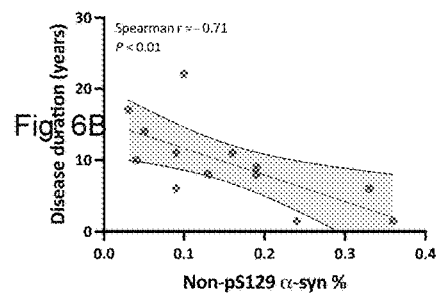
Figure 7C:
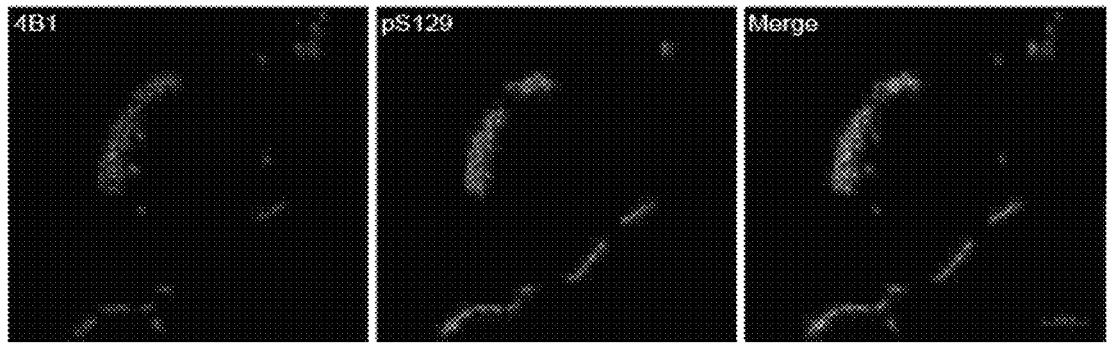

WT-α-Syn is Found in the Center of Most Lewy Pathological Lesions, and its Load Correlates Inversely with Disease Duration Immunohistochemical staining on PDD and DLB post-mortem human brain tissue demonstrated that WT-α-syn is found in Lewy neurites and Lewy bodies, though its load is approximately four-fold lower than total α-syn labelled by a pan-α-syn antibody (FIG. 7A). When normalized to total α-syn levels, there was no significant difference in load of either WT- or pS129-α-syn between Parkinson's disease dementia (PDD) and DLB cases, though WT-α-syn expression in the amygdala had a strong inverse relationship with disease duration across all cases (FIG. 7B). Using a Leica SP8 confocal microscope we performed z-stack image acquisition and 3D reconstruction using LasX software to determine the relative localization of non-phosphorylated S129 compared to pS129 α-syn. Using this method, we determined that the majority of α-synuclein accumulations consisted of a non-phosphorylated S129 core surrounded by pS129. Remarkably, confocal microscopy of PDD and DLB cases revealed a consistent picture of the core of most aggregates containing WT-α-syn, surrounded by a corona of pS129-α-syn (FIG. 7C). Overall, these findings support the suggestion that pS129 occurs secondarily to α-synuclein aggregation.

Example 12

Experimental Methods

Expression and Purification of Recombinant Human α-Syn
Full-length recombinant human α-syn was expressed in *Escherichia coli* BL21 (DE3) using the bacterial expression vector pRK172 (Vaikath et al., *Neuropathol Appl Neurobiol.* 45(6):597-608, 2019). Following expression and sedimentation, the bacterial pellets from 1 liter of Terrific broth (TB) were homogenized and sonicated in 50 ml of high-salt buffer (0.75 M NaCl, 10 mM Tris, pH 7.6, 1 mM EDTA) containing a cocktail of protease inhibitors (Thermo Scientific), heated to 100° C. for 10 min, and centrifuged at 5300 g for 20 min. The solution was dialyzed overnight against the buffer used for gel filtration chromatography (50 mM NaCl, 10 mM Tris, pH 7.6, 1 mM EDTA), following which, the volume was reduced to 5 ml using a Pierce protein concentrator (10K MWCO; ThermoFisher Scientific) according to the manufacturer's instructions. All proteins were purified by size exclusion using a Superdex 200 gel filtration column (GE Healthcare). The clean fractions were pooled, exchanged with a buffer (10 mM Tris pH 7.6, 25 mM NaCl, 1 mM EDTA, 1 mM PMSF) for ion exchange chromatography by dialysis overnight, and were applied onto a HiTrap Q column (GE Healthcare) and eluted in 10 mM Tris pH 7.6 using a linear gradient of 0.025-1.0 M NaCl. For preparation of α-syn monomers, the protein went through 100 KDa filters to remove any high molecular weight proteins. Purified fractions were pooled, and protein concentrations were determined using the Pierce BCA protein assay kit (ThermoFisher Scientific).

In Vitro Phosphorylation of α-Syn
Purified α-syn was phosphorylated at S129 as described previously (Landeck et al., *Mol Neurodegener.* 11(61), 2016). Briefly, 1 μg of Polo-like kinase 2 (PLK2) protein was added to 1.44 mg/ml (100 μM) α-syn in kinase reaction buffer (20 mM HEPES, 1.09 mM ATP, 2 mM DTT, 10 mM $MgCl_2$, pH 7.4). The reaction mixture was incubated at 30° C. for 24 h.

Aggregation of α-Syn In Vitro
The purity of α-syn was >95% as estimated by SDS gels. The α-syn samples were placed in 1.5 ml sterile polypropylene tubes and sealed with parafilm, followed by incubation at 37° C. for several days with continuous shaking at 800 rpm in a Thermomixer (Eppendorf). The samples were collected at the indicated time points, while the aggregation of α-syn was monitored by Th—S binding assay. The samples were stored at −80° C. for future analyses. Recombinant monomeric α-syn was mixed with various percentages of in vitro prepared monomeric pS129-α-syn (100, 50, 20, 5 or 0%) in 1.5 ml sterile polypropylene tubes, followed by incubation for up to twenty days.

Thioflavin-S(Th—S) Assay
A Th—S binding assay was used to study α-syn fibril formation. Being a fluorescent dye, Th—S interacts with fibrils containing β-sheet structures. The sample (10 μl) was diluted in 40 μl of Th—S(20 μM) in PBS and the mixture was dispensed in a 384-well, untreated black microplate (Nunc). Fluorescence was measured in a microplate reader (Perkin Elmer Envision) with the excitation and emission wavelengths at 450 and 510 nm, respectively.

Preparation of α-syn pure fibrils and pure seeds

Monomeric α-syn (100 μM) was aggregated as described above for 7 days. For preparation of pure fibrils, the crude α-syn fibril sample was spun at 10,000×g for 10 min at 4° C. in a refrigerated microfuge (Eppendorf). The supernatant was then discarded, and the pellet was washed twice and finally resuspended in1XPBS. For preparation of pure seeds, the pure fibrils were fragmented by ultrasonication while kept on ice using a Sonic ruptor 250, equipped with a fine tip (2 second pulses, output.of 40 watts for 5 min). For measurement of α-syn concentration of both fibrils and seeds, the samples were denatured with equal volume of 6

M Guanidine-HCl and quantified using Pierce BCA protein assay kit (ThermoFisher Scientific).

Seeded Polymerization Assay

The aggregation of monomeric WT- or pS129-α-syn with or without addition of seeds was conducted as previously described (Di Giovanni et al., *J Biol Chem.* 285(20):14941-14954, 2010). The seeds (WT or pS129) were prepared by fragmenting mature α-syn fibrils via sonication. Monomeric α-syn (100 µM) was seeded with different seed concentrations under incubation at 37° C. with continuous shaking. The fibril formation was assessed by the Th—S binding assay.

Isolation of TBS-Soluble Fraction from Brain Tissues

Brain tissues derived from the temporal and frontal cortex were homogenized on ice with a glass tissue homogenizer at 10% (w/v) in TBS (20 mM Tris-HCl pH 7.4, 150 mM NaCl) and 5 mM EDTA with protease and phosphatase inhibitors (ThermoFisher Scientific). Samples were centrifuged at 3000×g, at 4° C. for 30 min. The collected supernatant represents the TBS-soluble fraction. The total protein concentration was measured by BCA assay (ThermoFisher Scientific). Aliquots of 0.1 mg/mL were prepared and stored at −80° C.

Real Time Quaking-Induced Conversion (RT-QuIC) Assay

The RT-QuIC reaction buffer was composed of 0.1 M PIPES (pH 6.9), 0.1 mg/ml recombinant α-syn and 10 µM thioflavin-T (Th-T). Reactions were performed in triplicates in a black 96-well microplate with a clear bottom (Nunc) with 85 µl of the reaction mix loaded into each well together with 15 µl of 0.1 mg/ml TBS-soluble fractions. The plate was then sealed with a sealing tape (ThermoFisher) and incubated at 37° C. for 120 h in a BMG FLUOstar OMEGA plate reader with intermittent cyclesof 1 min shaking (500 rpm, double orbital) and 15 min rest throughout the indicated incubation time. Th-T fluorescence measurement, expressed as arbitrary relative fluorescence units (RFU), was taken with a bottom read every 15 min using 450±10 nm (excitation) and 480±10 nm (emission) wavelengths. A positive RT-QuIC signal was defined as RFU more than 5 standard deviation units (RFU>5 SD) above the mean of initial fluorescence at 120 h. The sample was considered positive if two or more of the replicates were positive, otherwise the sample was classified as negative.

RT-QuIC Data Analysis

The relative seeding activities of the assayed samples were presented by graphing fluorescence readouts against assay time. For each sample, we calculated three quantitative measures that can be used to analyze the RT-QuIC data: (1) the lag-phase (RFU>5 SD); (2) the amyloid formation rate, expressed as the inverse (1/time to threshold) of the lag-phase (Kang et al., *Biomed Res Int.* 2017(5413936), 2017), (3) and the maximum fluorescence value (FMAX) measured at the end of the RT-QuIC reaction. For the RT-QuIC negative samples, the lag-phase was assigned as 150 hours.

Tissue Culture of WT BE(2)-M17 Human Neuroblastoma Cells

Human neuroblastoma cells (WT BE(2)-M17) were cultured in Dulbecco's MEM/Nutrient Mix F-12 (1:1) (Hyclone) containing 10% FBS (Hyclone) and 1% penicillin-streptomycin (P/S; 10,000 U/ml penicillin, 10 mg/ml streptomycin, Sigma). The cells were maintained at 37° C. in a humidified incubator with 5% $CO_2$/95% air.

Tissue Culture of WT SH-SY5Y Human Dopaminergic Neuroblastoma Cells

Human dopaminergic neuroblastoma cells (WT SH-SY5Y) were cultured in Dulbecco's MEM/Nutrient Mix F-12 (1:1) containing 15% FBS, 1% penicillin-streptomycin (P/S; 10,000 U/ml penicillin, 10 mg/ml streptomycin), and supplemented with 1% non-essential MEM amino acid supplement (Gibco) and 2 mM freshly prepared glutamine. The cells were maintained at 37° C. in a humidified incubator with 5% $CO_2$/95% air.

Measurement of Cell Viability

To assess the cytotoxic effect of different α-syn species, cells were plated at a density of 15,000 cells (100 µl/well) in a 96-well plate. After 24 hours, the medium was replaced with 100 µl of MEM-RS (Hyclone) serum-free medium containing different solutions of α-syn species and treated for 48 hours. A total of 20 µl of 3-(4,5-dimethylthiazol-2-yl)-2,5-diphenyltetrazolium bromide MTT) (Sigma-Aldrich) (6 mg/ml) was dispensed into each well, and incubated for 4.5 h. This was replaced with 100 µl/well of lysis buffer (15% SDS, 50% N, N-dimethylformamide, pH 4.7) overnight. The absorbance values at 590 nm were measured in a microplate reader (Perkin Elmer). For experiments assessing the toxic effect of seeded polymerization, cells were treated in serum-free medium containing different solutions of α-syn species (pure fibrils and pure seeds) for 1 hour and monomeric α-syn was then added, followed by 48 hours incubation. Seeds (short fibrils) used in this experiment, were obtained upon sonication of α-syn fibrils.

HEK293-α-Syn-EGFP Cell Line Generation

Human embryonic kidney cells 293 (HEK293) were transfected with a plasmid encoding human WT-α-syn fused to EGFP, at the C-terminus, driven by the cytomegalovirus (CMV) promoter. The plasmid contained a selection marker for the antibiotic geneticin (G418) which was used for the selection of the stable transformants. Protein expression was confirmed by western blot analysis and fluorescence microscopy. A clonal HEK293-α-syn-EGFP cell line was selected and used for subsequent experiments. Cells were maintained in DMEM media supplemented with 10% Fetal Bovine Serum Gold (FBS) (PAA) and 1% Penicillin-Streptomycin (PAN). The cells were grown at 37° C. in an atmosphere of 5% CO2. For the seeding experiments, cells were plated on 13 mm glass coverslips in 24-well plates and incubated in 5% FBS-media. The following day, α-syn seeds were prepared in reactions of 150 µl per tube diluted in PBS, fragmented by sonication (Volpicelli-Daley et al., *Nat Protoc.* 9(9):2135-2146, 2014) and then added to cells at final concentration of 100 nM. Control cells were exposed to vehicle only (PBS). Cells were further incubated for 4 days, washed with PBS and fixed with 4% PFA for 20 min at room temperature (RT), followed by nuclei staining with 4'6'-diamidino-2-phenylindol (DAPI, Sigma-Aldrich, D8417) (1:5000 in DPBS) for 10 min. After a final wash, coverslips were mounted using Mowiol (Sigma-Aldrich) and subjected to fluorescence microscopy. The proportion of cells with α-syn inclusions within the population was then determined by counting. For quantification of aggregation, at least 200 cells were counted per variant and per experiment. Images were acquired using a 63× objective, and analyzed using LAS AF v.2.2.1 (Leica Microsystems) software.

Generation of 4-Oxo-2-Nonenal (ONE)-, 4-Hydroxy-2-Nonenal (HNE)-α-Syn Oligomers

HNE-/ONE-α-syn oligomers were prepared as previously described (Duffy et al., *Free Radic Biol Med.* 50(3):428-437, 2011). For generation of HNE-/ONE-α-syn oligomers, α-syn was dialysed against 50 mM disodium hydrogen phosphate, pH 8.5 followed by filtration using 100-kDa MWCO micron spin filter (Millipore) to get rid of high molecular weight aggregates. HNE or ONE (Abcam) was then added to α-syn monomers (140 µM) to get a final molar ratio of 30:1 (HNE/ONE: α-syn) followed by incubation of the samples at 37° C. for 18 hours without shaking. The samples were then centrifuged at 16,900×g for 5 min to remove any high molecular aggregated species. The supernatant containing theoligomeric species was then purified by size exclusion chromatography on a Superdex 200 gel filtration column (GE healthcare) equilibrated with 20 mM Tris pH 7.4, 0.15 M NaCl buffer. The eluted peaks fractions corresponding to the oligomeric fraction were pooled and quantified using BCA protein assay kit after solubilizing the oligomers in equal volume on 6 M GnHCl.

Filter Retardation Assay

Filter retardation assay was performed using a Minifold 48 slots (GE Healthcare Life Sciences). Each protein (50 µl) at a final concentration of 1 µg/ml was loaded into each slot on a nitrocellulose membrane that has been pre-soaked in PBS. Samples were allowed to absorb onto the nitrocellulose membrane and then slots were washedwith 1 ml of PBS. Membranes were then probed with relevant antibodies, and developed with SuperSignal West Pico Chemiluminescent Substrate Kit.

Inhibition ELISA

A 384-well black MaxiSorb microplate (Nunc) was coated with 1 µg/ml of α-syn monomers in 0.2 M NaHCO$_3$ pH 9.6 with overnight incubation at 4° C. 4B1 antibodyat 50 ng/ml was pre-incubated with serial dilutions of α-syn monomers or aggregates with continuous rolling for 2 hours. The antibody-protein mixture was then loaded to the antigen-coated plate and incubated for 10 min at RT. After washing step, goat anti-mouse IgG-RP (1:20,000, Jackson ImmunoResearch) was added for 1 hour to be later detected using SuperSignal ELISA Femto Chemiluminescent Substrate Kit.

Sandwich ELISA

A 384-well ELISA microplate was coated with 4B1 antibody at 0.5 µg/ml overnight at 4° C. in 0.2 M NaHCO$_3$ pH 9.6. After incubating the plate with 100 µl/well of blocking buffer for 2 hours at 37° C., serial dilutions of α-syn monomers, pS129-α-syn monomers, or different α-syn oligomers were added to corresponding wells, and incubated overnight at 4° C. Biotinylated 11D12 (mouse mAb for total α-syn) (Majbour et al., *Mol Neurodegener.* 11(7), 2016) was added as detection antibody and incubated at 37° C. for 2 hours followed by a washing step and incubation for 1 hour at 37° C. with streptavidin-HRP (Sigma). The plate was then washed and 50 µl/well of an enhanced chemiluminescent substrate (SuperSignal ELISA Femto, Pierce Biotechnology) was added to corresponding wells. The chemiluminescence, expressed in relative light units, was immediately measured using Envision plate reader (PerkinElmer Envision).

Tissue Culture of HEK 293 Human Embryonic Kidney Cells

WT HEK293cells were grown in Dulbecco's MEM-high glucose (Gibco) supplemented by 15% FBS (Gibco) and 1% penicillin-streptomycin (Gibco) and incubated at 37° C. in a 5% CO$_2$/95% air humidified incubator. After plating HEK cells overnight in 6-well plates, cells were transfected with 2 µg of WT-α-syn plasmid DNA by lipofectamine 3000 reagent (Invitrogen) (Stoppini et al., *J Neurosci Methods.* 37(2):173-182, 1991). One group of α-syn expressing HEK cells was similarly transfected again with 4 µg of mutant serine 129 to alanine (S129A) seeds the following day.

HEK cells were lysed, at 6, 12, 24, and 48 hours post seed transfection, initially with 1% Trition X-100 in 50 mM Tris, 150 mM NaCl (pH 7.6) containing protease and phosphatase inhibitors to obtain soluble fractions. The pellet was further lysed with 1% SDS in 50 mM Tris, 150 mM NaCl (pH 7.6) with complete inhibitors to attain insoluble fractions. Protein concentration was determined by BCA protein assay (Pierce) prior to analysis on 12% SDS-PAGE and immunoprobing with appropriate antibodies. These include monoclonal antibodies against rabbit pS129-α-syn (AB51253, Abcam), mouse α-syn Syn1 (610786) (BD Biosciences), and non-pS129-α-syn (4B1) in addition to antibody C4 against β-Actin (Sc-47778) (Santa Cruz Biotechnology) to normalize or the amount of proteins. Blots were subsequently incubated with horseradish peroxidase conjugated with anti-rabbit and anti-mouse IgG (Jackson ImmunoResearch), and proteins were detected with LiCOR system.

Organotypic Hippocampal Culture Slices (OHCS)

Organotypic hippocampal slice cultures were created from P7 C57B16/J mouse pups and injected with S129A-mutated human α-syn pre-formed fibrils as previously described (Elfarash et al., *Acta Neuropathol Commun.* 7(213), 2019), and cultured according to Stoppini et al. (*J Neurosci Methods.* 37(2):173-182, 1991). At various time points, tissue was fixed according to Gogolla et al. (*Nat Protoc.* 1(5):2452-2456, 2006) and stored at 4° C. until all tissue had been collected. Slices were permeabilized in 0.5% triton X-100 in PBS and blocked in 10% BSA. Primary antibodies against pS129-α-syn (D1R1R, Cell Signaling, #23706, 1:1000) and non-pS129-α-syn (4B1, 200 ng/mL) were diluted in 5% BSA and applied overnight at 4° C. After washing 6×15 min in 1×TBS+0.3% triton X-100, appropriate secondary Alexa-Fluor antibodies were diluted 1:2000, and DAPI 1:1000, in 5% BSA and applied for 3 hours at RT. Washing was repeated and slices were mounted using DAKO Fluorescent Mounting Medium (DAKO, S3023).

Immunofluorescence was evaluated on a Zeiss AxioObserver 7 inverted microscope fitted with an ApoTome to increase Z-plane resolution. For quantification of the distribution of pS129-α-syn vs. WT-α-syn in aggregates, ×63 images covering the aggregates were taken (5-20 images/slices depending on the amount of aggregation). Images were analyzed in ImageJ (NIH) in order to compute total phosphorylated and non-phosphorylated aggregate area proportions and mean fluorescence intensity of pS129 aggregates and WT-α-syn aggregates, as well as analyses stratified by aggregate morphology (small, intermediate and long Lewy-neurite-like plus cell body aggregates) and subregion localization.

Wild-Type Mice Injected with Recombinant α-Syn Pre-formed Fibrils (PFFs)

Wild-type C57B16 mice 2-4 months old (Jackson Laboratory) were housed in the animal facility of the Biomedical Research Foundation at the Academy of Athens in a room with a controlled light-dark cycle (12 hour light-12 hour dark) and free access to food and water. Adult male wild-type C57B16 mice were subjected to unilateral striatal injections under general isoflurane anesthesia by an apparatus adjusted to the stereotaxic frame (Kopf Instruments). Right dorsal striatum was targeted using the following coordinates from bregma: anteriorposterior+0.5 mm, mediolateral −1.4 mm and dorsoventral in two depths −3.2 mm and −3.4 mm according to mouse brain atlas. A total of 2.6 µg (2 µl) of mouse recombinant α-syn PFFs were injected at a constant flow rate of 0.3 µl/min. Equal volume of dPBS1× was used for control animals. An interval of 5 min was maintained between the two dorsoventral depths and the needle was slowly removed 5 min after the injection procedure was completed. For immunohistochemical analysis, mice were transcardially perfused under isoflurane anaesthesia, followed by ice-cold 4% paraformaldehyde (PFA), 2 weeks post stereotaxic injections. Following fixation, the brains were dehydrated by sequential incubation in 15% and 30% sucrose, snap frozen in isopentane at −50° C. and stored at −80° C. Free-floating cryostat-cut coronal sections (30 µm) covering the whole nigrostriatal axis were stained with antibodies against pS129-α-syn, 4B1, and DAT. The sections were treated with antigen retrieval solution (citrate buffer, pH=6) at 80° C. for 20 min. To validate whether pS129-positive α-syn accumulations were proteinase K (PK) resistant, sections were incubated with PK (Sigma-Aldrich) 2.5 µg/ml in PBS for 10 min at 25° C. Fluorescent images were obtained in a Leica SP5-II confocal microscope. A protocol with sequential image acquisition was used.

Immunohistochemistry and Immunofluorescence

Formalin-fixed paraffin-embedded brain tissue from the amygdala was obtained post-mortem from patients with PD dementia and DLB. Sections (6 µm) were cut and stained with 4B1, pS129 or pan-α-syn (KM51, Leica Novocastra) antibodies and detected using conventional immunohistochemistry. Regions of interest were imaged on a Zeiss A.1 microscope from five (amygdala) regions and percentage area immunoreactive was evaluated using ImagePro software. The same regions were evaluated on serial sections with different antibodies and compared between cases and across sections, and compared to clinical data obtained during life. 4B1 and pS129 antibodies were co-stained on sections for immunofluorescent analysis using a Leica SP8 confocal microscope. LasX software was used to generate three-dimensional images from z-stacked data to determine whether or not the core of aggregates was phosphorylated at serine 129.

Statistical analyses

Statistical analyses were done using the Student's t-test for independent variables. Using the GraphPad Prism software (version 8.3.0), statistical analysis was performed using one-way ANOVA, followed by Tukey's multiple comparison test for the MTT cell viability, Th—S, and RT-QuIC assays or followed by the Holm-Sidek test for the OHCS. The data are presented as mean±standard deviation and represents results from at least 3 independent experiments.

Example 13

Sequence of mAb 4B1

Total RNA was isolated from mAb 4B1 hybridoma cells following the technical manual of the Monarch® Total RNA Miniprep Kit (New England Biolabs, Ipswich, MA). Total RNA was then reverse-transcribed into cDNA using switching mechanism at 5' end of RNA transcript technology. The variable region of the antibody was amplified and cloned separately in a standard cloning vector, and then sequenced using Sanger sequencing technology.

The cDNA sequence of the heavy chain was determined to be:

(SEQ ID NO: 4)
ATGAATTTCGGGCTCAGCTTGATTTTCCTTGTCCCTGTTTTAAAAGGTGT

CCTGTGTGAAGTGAAACTGGTGGAGTCTGGGGGAGGTTTAGTGCAGCCTG

GAGGGTCCCTGAAACTCTCCTGTGCAGCCTCTGGAATCACTTTCAGTAGC

TATACCATGTCTTGGGTTCGCCAGACTCCAGAGAAGAGGCTGGAGTGGGT

CGGATATATTAGTAATGGTGGTGGTAGGACCTACTATCCAGACACTGTAA

AGGGCCGATTCACCATCTCCAGAGACAATGCCAAGAACACCCTGTACCTG

CAAATGAGCAGTCTGAAGTCTGAGGACACGGCCATGTATTACTGTGCAAG

ACAGATTACTACGGCTATGGGGTATTACTATGCTATGGACTACTGGGGTC

AAGGAACCTCAGTCACCGTCTCCTCA*GCCAAAACGACACCCCCATCTGTC*

*TATCCACTGGCCCCTGGATCTGCTGCCCAAACTAACTCCATGGTGACCCT*

*GGGATGCCTGGTCAAGGGCTATTTCCCTGAGCCAGTGACAGTGACCTGGA*

*ACTCTGGATCCCtgtccagcggtgtgcacaccttcccagctgtcctggag*

*tctgacctctacactctgagcagctcagtgactgtcccctccagccctcg*

*gcccagcgagaccgtcacctgcaacgttgcccacccggccagcagcacca*

*aggtggacaagaaaattgtgcccagggattgtggttgtaagccttgcata*

*tgtacagtcccagaagtatcatctgtcttcatcttcccccccaaagcccaa*

*ggatgtgctcaccattactctgactcctaaggtcacgtgtgttgtggtag*

*acatcagcaaggatgatcccgaggtccagttcagctggtttgtagatgat*

*gtggaggtgcacacagctcagacgcaaccccgggaggagcagttcaacag*

*cacttcccgctcagtcagtgaacttccatcatgcaccaggactggctca*

*atggcaaggagttcaaatgcagggtcaacagtgcagctttccctgccccc*

*atcgagaaaaccatctccaaaaccaaaggcagaccgaaggctccacaggt*

*gtacaccattccacctcccaaggagcagatggccaaggataaagtcagtc*

*tgacctgcatgataacagacttcttccctgaagacattactgtggagtgg*

*cagtggaatgggcagccagcggagaactacaagaacactcagcccatcat*

*gaacacgaatggctcttacttcgtctacagcaagctcaatgtgcagaaga*

*gcaactgggaggcaggaaatactttcacctgctctgtgttacatgagggc*

*ctgcacaaccaccatactgagaagagcctctcccactctcctggtaaatg*

*a.*

The heavy chain cDNA sequence (SEQ ID NO: 4) is 1401 bases in length, including the termination codon. The beginning of sequence encodes the signal peptide. The underlined sequence encodes the variable region of the heavy chain, consisting of framework and CDRs, and the CDR-encoding portions are in boldface. The designation of framework and CDRs is according to the IMGT delineation system. The italicized text indicates the constant region-encoding segment of the cDNA; the portion in lower case was taken from published sequence rather than being re-determined. Sequence analysis using NCBI Ig-BLAST indicates that: the germline V-gene was IGVH5-12-2*01 or possibly IGVH5-12*01 or IGVH5-12*02; the germline D gene was IGHD1-2*01; and the germline J gene was IGHJ4*01. SEQ ID NO:4 and the regions identified therein constitute means for encoding the heavy chain, the heavy chain variable and constant regions, the heavy chain signal sequence, and the heavy chain CDRs of an antibody that specifically binds aggregated, non-phosphorylated α-synuclein.

The heavy chain cDNA encodes a 466 residue amino acid sequence:

(SEQ ID NO: 5)
MNFGLSLIFLVPVLKGVLCEVKLVESGGGLVQPGGSLKLSCAASGITFSS

YTMSWVRQTPEKRLEWVGYISNGGGRTYYPDTVKGRFTISRDNAKNTLYL

-continued

QMSSLKSEDTAMYYCARQITTAMGYYYAMDYWGQGTSVTVSS*AKTTPPSV*

*YPLAPGSAAQTNSMVTLGCLVKGYFPEPVTVTWNSGSlssgvhtfpavlq*

*sdlytlsssvtvpssprpsetvtcnvahpasstkvdkkivprdcgckpci*

*ctvpevssvfifppkpkdvltitltpkvtcvvvdiskddpevqfswfvdd*

*vevhtaqtqpreeqfnstfrsyselpimhqdwlngkefkcrvnsaafpap*

*iektisktkgrpkapqvytipppkeqmakdkvsltcmitdffpeditvew*

*qwngqpaenykntqpimntngsyfvysklnvqksnweagntftcsvlheg*

*lhnhhtekslshspgk.*

As above, the variable region, consisting of framework and CDRs, is underlined and the CDRs are in boldface. The italicized text indicates the constant region; the portion in lower case was based on published sequence.

The heavy chain variable region sequence is:

(SEQ ID NO: 6)
EVKLVESGGGLVQPGGSLKLSCAASGITFSSYTMSWVRQTPEKRLEWVGY

ISNGGGRTYYPDTVKGRFTISRDNAKNTLYLQMSSLKSEDTAMYYCARQI

TTAMGYYYAMDYWGQGTSVTVSS

The heavy chain CDRs are:

(SEQ ID NO: 7)
HCDR1: GITFSSYT, (SEQ ID NO: 8)
HCDR2: ISNGGGRT, and (SEQ ID NO: 9)
HCDR3: ARQITTAMGYYYAMDY.

The light chain cDNA sequence of the light chain was determined to be:

(SEQ ID NO: 10)
ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTGTACAC

AGTAATGGAAACACCTATTTACATTGGTACCTGCAGAAGCCAGGCCAGTC

TCCGAAGCTCCTGATCTCCAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTTCTGCTCTCAAAGTACACA

TGTTCCGCTCACGTTCGGTGCTGGGACCAAGCTGGAGCTGAAA*CGGGCTG*

*ATGCTGCACCAACTGTATCCATCTTCCCACCATCCAGTGAGCAGTTAACA*

*TCTGGAGGTGCCTCAGTCGTGTGCTTCTTGAACAACTTCTACCCCAAAGA*

*CATCAATGTCAAGTGGAAGATTGATGGCAGTGAACGACAAAATGGCGTCC*

*TGAACAGTTGGACTGATCAGGACAGCAAAGACAGCACCTACAGCATGAGC*

*AGCACCCTCACGTTGACCAAGGACGAGTATGAACGACATAACAGCTATAC*

*CTGTGAGGCCACTCACAAGACATCAACTTCACCCATTGTCAAGAG*ct tca

*acaggaatgagtgttag.*

The light chain cDNA sequence (SEQ ID NO: 10) is 717 bases in length, including the termination codon. The beginning of sequence encodes the signal peptide. The underlined sequence encodes the variable region of the light chain, consisting of framework and CDRs, and the CDR-encoding portions are in boldface. The designation of framework and CDRs is according to the IMGT delineation system. The italicized text indicates the constant region-encoding segment of the cDNA; the portion in lower case was taken from published sequence rather than being re-determined. Sequence analysis using NCBI Ig-BLAST indicates that this is a kappa light chain and the germline V-gene was IGKV1-110*01, IGKV1-110*02, or IGKV1-117*01, and the germline J gene was IGKJ5*01. SEQ ID NO:10 and the regions identified therein constitute means for encoding the light chain, the light chain variable and constant regions, the light chain signal sequence, and the light chain CDRs of an antibody that specifically binds aggregated, non-phosphorylated α-synuclein.

The light chain cDNA encodes a 238 residue amino acid sequence:

(SEQ ID NO: 11)
MKLPVRLLVLMFWIPASSSD*VVMTQTPLSLPVSLGDQASISCRSS**QSLVH*

*SNGNTYLHWYLQKPGQSPKLLISKVSNRFSGVPDRFSGSGSGTDFTLKIS*

*RVEAEDLGVYFCSQSTHVPLTF*GAGTKLELK*RADAAPTVSIFPPSSEQLT*

*SGGASVVCFLNNFYPKDINVKWKIDGSERQNGVLNSWTDQDSKOSTYSMS*

*STLTLTKDEYERHNSYTCEATHKTSTSPIVKsfnrnec*

The light chain variable region sequence is:

(SEQ ID NO: 12)
DVVMTQTPLSLPVSLGDQASISCRSSQSLVHSNGNTYLHWYLQKPGQSPK

LLISKVSNRFSGVPDRFSGSGSGTDFTLKISRVEAEDLGVYFCSQSTHVP

LTFGAGTKLELK.

The light chain CDRs are:

(SEQ ID NO: 13)
LCDR1: QSLVHSNGNTY, (SEQ ID NO: 14)
LCDR2: KVS, and (SEQ ID NO: 15)
LCDR3: SQSTHVPLT.

EXEMPLARY EMBODIMENTS

Embodiment 1. A hybridoma cell line as deposited with the American Type Culture Collection under patent deposit accession number PTA-127017.

Embodiment 2. A monoclonal antibody produced by the hybridoma of Embodiment 1.

Embodiment 3. A hybridoma generated by a method comprising immunizing a mouse with a peptide comprising amino acid residues 125-133 of α-synuclein (SEQ ID NO: 1).

Embodiment 4. The hybridoma of claim 3, wherein the peptide comprising amino acid residues 125-133 of α-synuclein is CYEMPSEEGY (SEQ ID NO: 3).

Embodiment 5. A monoclonal antibody produced by the hybridoma of Embodiment 3.

Embodiment 6. A monoclonal antibody made by a process comprising immunizing a laboratory animal with means for inducing antibodies recognizing aggregated, non-phosphorylated α-synuclein.

Embodiment 7. The monoclonal antibody of Embodiment 6, wherein the laboratory animal is a mouse.

Embodiment 8. The monoclonal antibody of Embodiment 6, wherein the means for inducing antibodies recognizing aggregated, non-phosphorylated α-synuclein are conjugated to a carrier protein.

Embodiment 9. The monoclonal antibody of Embodiment 8, wherein the carrier protein is keyhole limpet hemocyanin.

Embodiment 10. The monoclonal antibody of Embodiment 6, wherein he means for inducing antibodies recognizing aggregated, non-phosphorylated α-synuclein is the peptide CYEMPSEEGY (SEQ ID NO:3).

Embodiment 11. The monoclonal antibody of Embodiment 2 that is a fragment of a whole antibody.

Embodiment 12. An immunoassay for the detection or quantitation of aggregated, non-phosphorylated α-synuclein comprising a step for contacting a sample with means for binding WT-α-syn.

Embodiment 13. The immunoassay of Embodiment 12, wherein the means for binding WT-α-syn is the monoclonal antibody produced by the hybridoma deposited with the American Type Culture Collection under patent deposit accession number PTA-127017.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The 19 KB ASCII text file named 5600234-00619 Sequence Listing_ST25.txt created 10/14/2021 is incorporated herein by reference.

The invention claimed is:

1. A monoclonal antibody that specifically binds aggregated, non-phosphorylated α-synuclein comprising a heavy chain variable region (VH) and a light chain variable region (VL), wherein:
   i. the VH comprises heavy chain complementarity determining regions (HCDRs) 1-3 having the amino acid sequences of SEQ ID NOs:7-9, respectively; and
   ii. the VL comprises light chain complementarity determining regions (LCDRs) 1-3 having the amino acid sequences of SEQ ID NOs:13-15, respectively.

2. The monoclonal antibody of claim 1, wherein the antibody is an intact antibody.

3. The monoclonal antibody of claim 1, wherein VH comprises the amino acid sequence of SEQ ID NO:6 and VL comprises the amino acid sequence of SEQ ID NO:12.

4. The monoclonal antibody of claim 3, wherein the antibody is an intact antibody.

* * * * *